US006849715B2

(12) United States Patent
Von Eichel-Streiber et al.

(10) Patent No.: US 6,849,715 B2
(45) Date of Patent: Feb. 1, 2005

(54) AGENTS USEFUL FOR INACTIVATION OF RAS SUBFAMILY PROTEINS

(75) Inventors: Christoph Von Eichel-Streiber, Schweppenhausen (DE); Patrice Boquet, Nice (FR); Monica Thelestam, Soina (SE)

(73) Assignee: Zentaris AG, Frankfurt (DE)

( * ) Notice: Subject to any disclaimer, the term of this patent is extended or adjusted under 35 U.S.C. 154(b) by 0 days.

(21) Appl. No.: 09/126,816

(22) Filed: Jul. 31, 1998

(65) Prior Publication Data

US 2003/0103987 A1 Jun. 5, 2003

Related U.S. Application Data

(63) Continuation of application No. PCT/EP97/00426, filed on Jan. 31, 1997.

(30) Foreign Application Priority Data

Feb. 2, 1996 (EP) .............................................. 96101469

(51) Int. Cl.[7] .............................. C07K 1/00; C12P 21/08
(52) U.S. Cl. ..................... 530/350; 530/825; 530/387.3
(58) Field of Search .............................. 530/350, 387.1, 530/825, 387.3, 341.7, 820; 424/133.1, 183.1, 134.1; 514/2

(56) References Cited

FOREIGN PATENT DOCUMENTS

WO          94/22476     * 10/1994

OTHER PUBLICATIONS

Popoff (Infection & Immunity, 1987, vol. 55, No. 1, pp. 35–43).*
Green et al. (Gene, 1995, vol. 161, pp. 57–61).*
Blakey et al. (Antibody Toxin Conjugates: A Perspective. Waldmann H. (ed): Monoclonal Antibody Thearpy.Prog.Allergy. Base Karger, 1988 vol. 45, pp. 50–90.*
Just et al. (Nature, vol. 375, Jun. 8, 1995, pp. 500–503).*
Rudikoff et al proc Natl Acad Sci USa vol. 79; 1979, 1982.*
Panka et al PNAS 85:3080, 5/88.*
Amit et al Science 233:747, 1986.*
Chaves–Olarte J BioChem 274(16)11046, 4/99.*
Von Eichel–Steiber et al Mol Microbiol vol. 17(2) 313, 1995.*
Vitetta et al Science 238:1038, 11/87.*
Sandhu Critical Reviews in Biotechnology vol. 12(4/5) 437, 1982.*

* cited by examiner

Primary Examiner—Gary B. Nickol
(74) Attorney, Agent, or Firm—Pillsbury Winthrop LLP

(57) ABSTRACT

A method of treating a disorder characterized by an activating mutation in a Ras proto-oncogene, comprising contacting cells of a patient suffering from the disorder with a protein having the toxic activity of *Clostridium sordellii* toxin LT under conditions favoring inactivation of Ras by glucosylation of Ras' threonine 35 in said cell. The protein preferably is an immunotoxin that contains as a toxic domain the catalytic domain of toxin LT.

5 Claims, 8 Drawing Sheets

1   2   3   4   5   6

48 kDa 22 kDa                Ral

Figure 1:
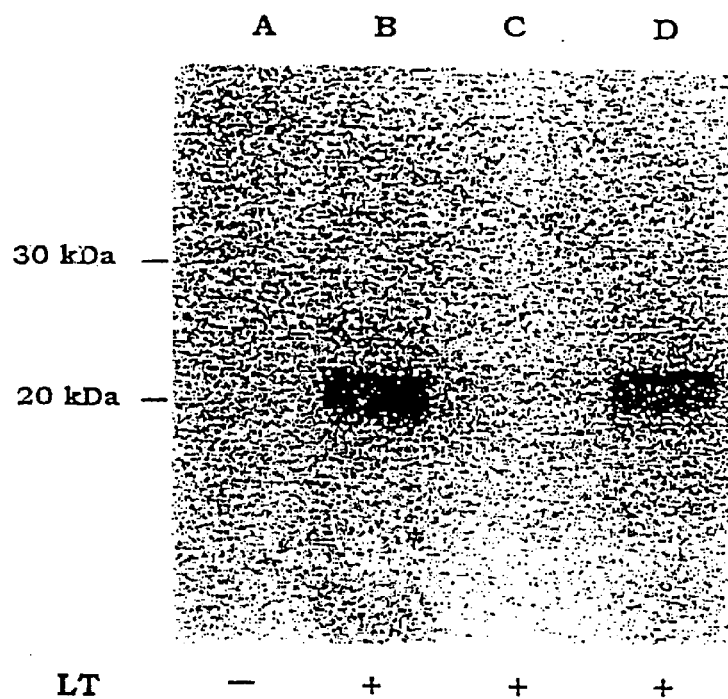

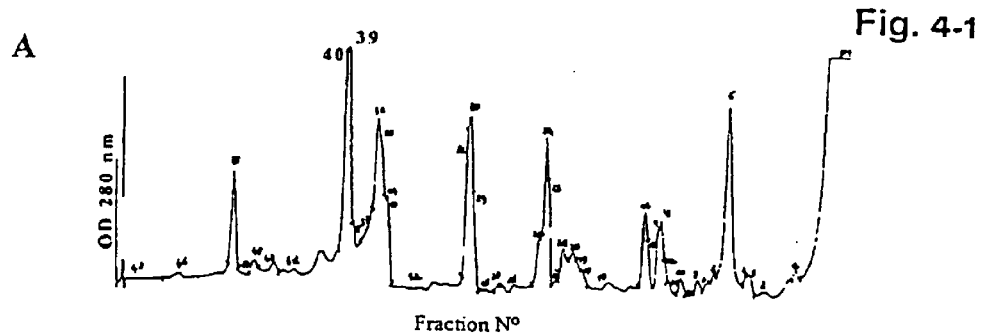
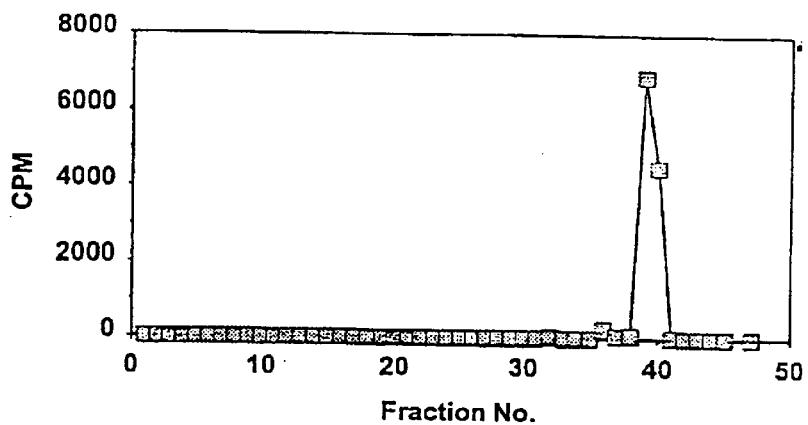
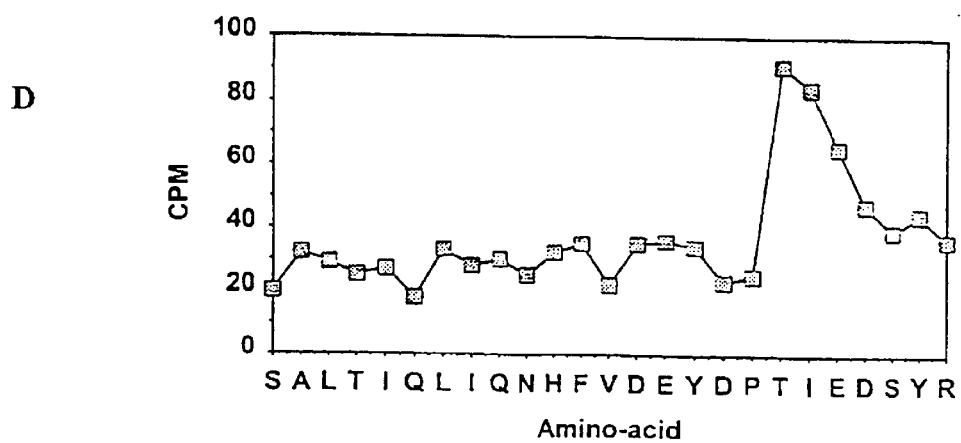
Fig. 4-1

Figure 2:
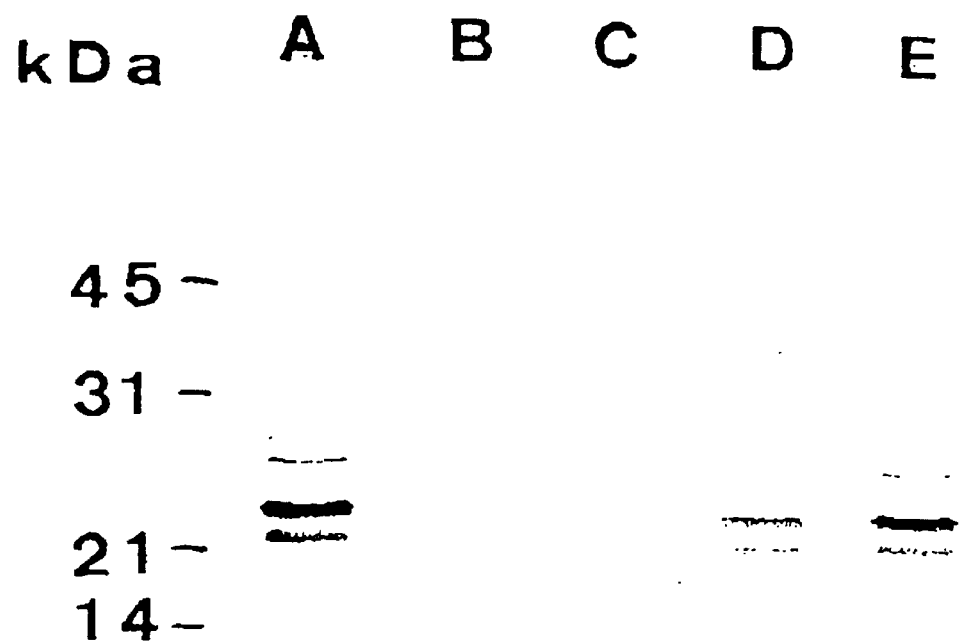

Fig. 4-2
B
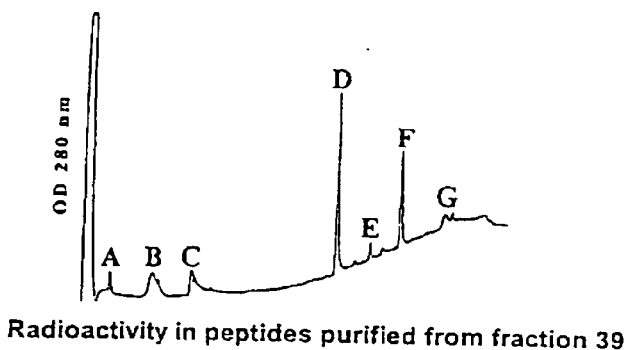
Radioactivity in peptides purified from fraction 39
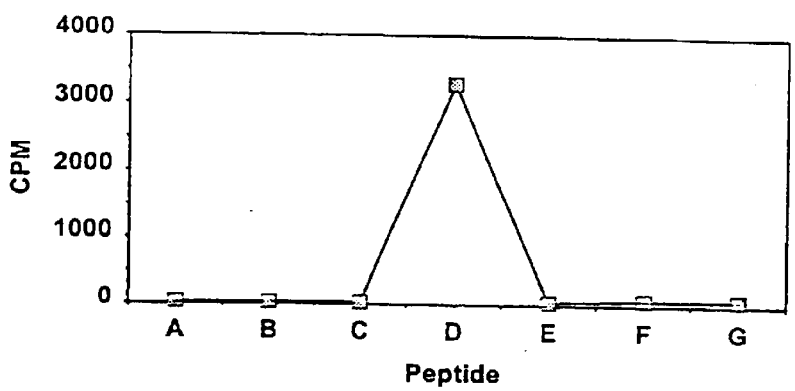
C
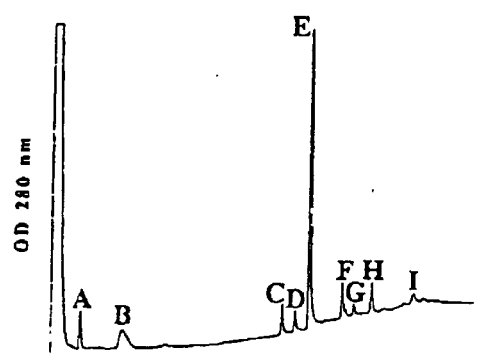
Radioactivity in peptides purified from fraction 40
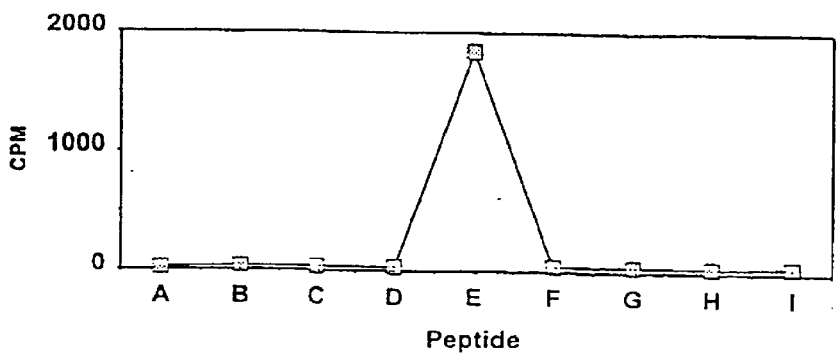

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1
ggggaatttt aatgagctca gttaacaaag c                                    31

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 2
ttcagataat gtaggtacca agtctatag                                       29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
ctatagactt ggtacctaca ttatctgaa                                       29

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer -continued

```
<400> SEQUENCE: 4
tattaacgtg ggcccaatat atgtctac                                              28

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Leu Thr Ile Gln Leu Ile Gln Asn His Phe Val Asp Glu Tyr
 1               5                  10                  15

Asp Pro Thr Ile Glu Asp Ser Tyr Arg
             20                  25

<210> SEQ ID NO 6
<211> LENGTH: 2364
<212> TYPE: PRT
<213> ORGANISM: Clostridium sordellii

<400> SEQUENCE: 6

Met Asn Leu Val Asn Lys Ala Gln Leu Gln Lys Met Val Tyr Val Lys
 1               5                  10                  15

Phe Arg Ile Gln Glu Asp Glu Tyr Val Ala Ile Leu Asn Ala Leu Glu
             20                  25                  30

Glu Tyr His Asn Met Ser Glu Ser Ser Val Val Glu Lys Tyr Leu Lys
         35                  40                  45

Leu Lys Asp Ile Asn Asn Leu Thr Asp Asn Tyr Leu Asn Thr Tyr Lys
     50                  55                  60

Lys Ser Gly Arg Asn Lys Ala Leu Lys Lys Phe Lys Glu Tyr Leu Thr
 65                  70                  75                  80

Met Glu Val Leu Glu Leu Lys Asn Asn Ser Leu Thr Pro Val Glu Lys
                 85                  90                  95

Asn Leu His Phe Ile Trp Ile Gly Gly Gln Ile Asn Asp Thr Ala Ile
            100                 105                 110

Asn Tyr Ile Asn Gln Trp Lys Asp Val Asn Ser Asp Tyr Thr Val Lys
        115                 120                 125

Val Phe Tyr Asp Ser Asn Ala Phe Leu Ile Asn Thr Leu Lys Lys Thr
    130                 135                 140

Ile Val Glu Ser Ala Thr Asn Asn Thr Leu Glu Ser Phe Arg Glu Asn
145                 150                 155                 160

Leu Asn Asp Pro Glu Phe Asp Tyr Asn Lys Phe Tyr Arg Lys Arg Met
                165                 170                 175

Glu Ile Ile Tyr Asp Lys Gln Lys His Phe Ile Asp Tyr Tyr Lys Ser
            180                 185                 190

Gln Ile Glu Glu Asn Pro Glu Phe Ile Ile Asp Asn Ile Ile Lys Thr
        195                 200                 205

Tyr Leu Ser Asn Glu Tyr Ser Lys Asp Leu Gly Leu Ala Leu Asn Lys Tyr
    210                 215                 220

Ile Glu Glu Ser Leu Asn Lys Ile Thr Ala Asn Asn Gly Asn Asp Ile
225                 230                 235                 240

Arg Asn Leu Glu Lys Phe Ala Asp Glu Asp Leu Val Arg Leu Tyr Asn
                245                 250                 255

Gln Glu Leu Val Glu Arg Trp Asn Leu Ala Ala Ala Ser Asp Ile Leu
            260                 265                 270
```

-continued

```
Arg Ile Ser Met Leu Lys Glu Asp Gly Val Tyr Leu Asp Val Asp
        275                 280                 285
Ile Leu Pro Gly Ile Gln Pro Asp Leu Phe Lys Ser Ile Asn Lys Pro
290                 295                 300
Asp Ser Ile Thr Asn Thr Ser Trp Glu Met Ile Lys Leu Glu Ala Ile
305                 310                 315                 320
Met Lys Tyr Lys Glu Tyr Ile Pro Gly Tyr Thr Ser Lys Asn Phe Asp
                325                 330                 335
Met Leu Asp Glu Glu Val Gln Arg Ser Phe Glu Ser Ala Leu Ser Ser
                340                 345                 350
Lys Ser Asp Lys Ser Glu Ile Phe Leu Pro Leu Asp Ile Lys Val
            355                 360                 365
Ser Pro Leu Glu Val Lys Ile Ala Phe Ala Asn Asn Ser Val Ile Asn
        370                 375                 380
Gln Ala Leu Ile Ser Leu Lys Asp Ser Tyr Cys Ser Asp Leu Val Ile
385                 390                 395                 400
Asn Gln Ile Lys Asn Arg Tyr Lys Ile Leu Asn Asp Asn Leu Asn Pro
                405                 410                 415
Ser Ile Asn Glu Gly Thr Asp Phe Asn Thr Thr Met Lys Ile Phe Ser
            420                 425                 430
Asp Lys Leu Ala Ser Ile Ser Asn Glu Asp Asn Met Met Phe Met Ile
        435                 440                 445
Lys Ile Thr Asn Tyr Leu Lys Val Gly Phe Ala Pro Asp Val Arg Ser
    450                 455                 460
Thr Ile Asn Leu Ser Gly Pro Gly Val Tyr Thr Gly Ala Tyr Gln Asp
465                 470                 475                 480
Leu Leu Met Phe Lys Asp Asn Ser Thr Asn Ile His Leu Leu Glu Pro
                485                 490                 495
Glu Leu Arg Asn Phe Glu Phe Pro Lys Thr Lys Ile Ser Gln Leu Thr
            500                 505                 510
Glu Gln Glu Ile Thr Ser Leu Trp Ser Phe Asn Gln Ala Arg Ala Lys
        515                 520                 525
Ser Gln Phe Glu Glu Tyr Lys Lys Gly Tyr Phe Glu Gly Ala Leu Gly
    530                 535                 540
Glu Asp Asp Asn Leu Asp Phe Ala Gln Asn Thr Val Leu Asp Lys Asp
545                 550                 555                 560
Tyr Val Ser Lys Lys Ile Leu Ser Ser Met Lys Thr Arg Asn Lys Glu
                565                 570                 575
Tyr Ile His Tyr Ile Val Gln Leu Gln Gly Asp Lys Ile Ser Tyr Glu
            580                 585                 590
Ala Ser Cys Asn Leu Phe Ser Lys Asp Pro Tyr Ser Ile Leu Tyr
        595                 600                 605
Gln Lys Asn Ile Glu Gly Ser Glu Thr Ala Tyr Tyr Tyr Val Ala
    610                 615                 620
Asp Ala Glu Ile Lys Glu Ile Asp Lys Tyr Arg Ile Pro Tyr Gln Ile
625                 630                 635                 640
Ser Asn Lys Arg Asn Ile Lys Leu Thr Phe Ile Gly His Gly Lys Ser
                645                 650                 655
Glu Phe Asn Thr Asp Thr Phe Ala Asn Leu Asp Val Asp Ser Leu Ser
            660                 665                 670
Ser Glu Ile Glu Thr Ile Leu Asn Leu Ala Lys Ala Asp Ile Ser Pro
        675                 680                 685
```

-continued

```
Lys Tyr Ile Glu Ile Asn Leu Leu Gly Cys Asn Met Phe Ser Tyr Ser
            690                 695                 700

Ile Ser Ala Glu Glu Thr Tyr Pro Gly Lys Leu Leu Lys Ile Lys
705                 710                 715                 720

Asp Arg Val Ser Glu Leu Met Pro Ser Ile Ser Gln Asp Ser Ile Thr
                725                 730                 735

Val Ser Ala Asn Gln Tyr Glu Val Arg Ile Asn Glu Glu Gly Lys Arg
            740                 745                 750

Glu Ile Leu Asp His Ser Gly Lys Trp Ile Asn Lys Glu Glu Ser Ile
                755                 760                 765

Ile Lys Asp Ile Ser Ser Lys Glu Tyr Ile Ser Phe Asn Pro Lys Glu
770                 775                 780

Asn Lys Ile Ile Val Lys Ser Lys Tyr Leu His Glu Leu Ser Thr Leu
785                 790                 795                 800

Leu Gln Glu Ile Arg Asn Asn Ala Asn Ser Ser Asp Ile Asp Leu Glu
                805                 810                 815

Lys Lys Val Met Leu Thr Glu Cys Glu Ile Asn Val Ala Ser Asn Ile
            820                 825                 830

Asp Arg Gln Ile Val Glu Gly Arg Ile Glu Ala Lys Asn Leu Thr
                835                 840                 845

Ser Asp Ser Ile Asn Tyr Ile Lys Asn Glu Phe Lys Leu Ile Glu Ser
850                 855                 860

Ile Ser Asp Ser Leu Tyr Asp Leu Lys His Gln Asn Gly Leu Asp Asp
865                 870                 875                 880

Ser His Phe Ile Ser Phe Glu Asp Ile Ser Lys Thr Glu Asn Gly Phe
                885                 890                 895

Arg Ile Arg Phe Ile Asn Lys Glu Thr Gly Asn Ser Ile Phe Ile Glu
            900                 905                 910

Thr Glu Lys Glu Ile Phe Ser Glu Tyr Ala Thr His Ile Ser Lys Glu
                915                 920                 925

Ile Ser Asn Ile Lys Asp Thr Ile Phe Asp Asn Val Asn Gly Lys Leu
930                 935                 940

Val Lys Lys Val Asn Leu Asp Ala Ala His Glu Val Asn Thr Leu Asn
945                 950                 955                 960

Ser Ala Phe Phe Ile Gln Ser Leu Ile Glu Tyr Asn Thr Thr Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ser Lys Val Val
                995                 1000                1005

Glu Leu Val Ser Thr Ala Leu Asp Glu Thr Ile Asp Leu Leu Pro Thr
     1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Asn Asp Pro Leu Leu
                1045                1050                1055

Arg Gln Glu Ile Glu Ala Lys Ile Gly Ile Met Ala Val Asn Leu Thr
            1060                1065                1070

Ala Ala Ser Thr Ala Ile Val Thr Ser Ala Leu Gly Ile Ala Ser Gly
                1075                1080                1085

Phe Ser Ile Leu Leu Val Pro Leu Ala Gly Ile Ser Ala Gly Ile Pro
     1090                1095                1100

Ser Leu Val Asn Asn Glu Leu Ile Leu Gln Asp Lys Ala Thr Lys Val
```

-continued

```
        1105                1110                1115                1120
Ile Asp Tyr Phe Lys His Ile Ser Leu Ala Glu Thr Glu Gly Ala Phe
                    1125                1130                1135
Thr Leu Leu Asp Asp Lys Ile Ile Met Pro Gln Asp Asp Leu Val Leu
            1140                1145                1150
Ser Glu Ile Asp Phe Asn Asn Asn Ser Ile Thr Leu Gly Lys Cys Glu
        1155                1160                1165
Ile Trp Arg Ala Glu Gly Gly Ser Gly His Thr Leu Thr Asp Asp Ile
    1170                1175                1180
Asp His Phe Phe Ser Ser Pro Ser Ile Thr Tyr Arg Lys Pro Trp Leu
1185                1190                1195                1200
Ser Ile Tyr Asp Val Leu Asn Ile Lys Lys Glu Lys Ile Asp Phe Ser
                1205                1210                1215
Lys Asp Leu Met Val Leu Pro Asn Ala Pro Asn Arg Val Phe Gly Tyr
            1220                1225                1230
Glu Met Gly Trp Thr Pro Gly Phe Arg Ser Leu Asp Asn Asp Gly Thr
        1235                1240                1245
Lys Leu Leu Asp Arg Ile Arg Asp His Tyr Glu Gly Gln Phe Tyr Trp
    1250                1255                1260
Arg Tyr Phe Ala Phe Ile Ala Asp Ala Leu Ile Thr Lys Leu Lys Pro
1265                1270                1275                1280
Arg Tyr Glu Asp Thr Asn Val Arg Ile Asn Leu Asp Gly Asn Thr Arg
                1285                1290                1295
Ser Phe Ile Val Pro Val Ile Thr Thr Glu Gln Ile Arg Lys Asn Leu
            1300                1305                1310
Ser Tyr Ser Phe Tyr Gly Ser Gly Gly Ser Tyr Ser Leu Ser Leu Ser
        1315                1320                1325
Pro Tyr Asn Met Asn Ile Asp Leu Asn Leu Val Glu Asn Asp Thr Trp
    1330                1335                1340
Val Ile Asp Val Asp Asn Val Val Lys Asn Ile Thr Ile Glu Ser Asp
1345                1350                1355                1360
Glu Ile Gln Lys Gly Glu Leu Ile Glu Asn Ile Leu Ser Lys Leu Asn
                1365                1370                1375
Ile Glu Asp Asn Lys Ile Ile Leu Asn Asn His Thr Ile Asn Phe Tyr
            1380                1385                1390
Gly Asp Ile Asn Glu Ser Asn Arg Phe Ile Ser Leu Thr Phe Ser Ile
        1395                1400                1405
Leu Glu Asp Ile Asn Ile Ile Ile Glu Ile Asp Leu Val Ser Lys Ser
    1410                1415                1420
Tyr Lys Ile Leu Leu Ser Gly Asn Cys Met Lys Leu Ile Glu Asn Ser
1425                1430                1435                1440
Ser Asp Ile Gln Gln Lys Ile Asp His Ile Gly Phe Asn Gly Glu His
                1445                1450                1455
Gln Lys Tyr Ile Pro Tyr Ser Tyr Ile Asp Asn Glu Thr Lys Tyr Asn
            1460                1465                1470
Gly Phe Ile Asp Tyr Ser Lys Lys Glu Gly Leu Phe Thr Ala Glu Phe
        1475                1480                1485
Ser Asn Glu Ser Ile Ile Arg Asn Ile Tyr Met Pro Asp Ser Asn Asn
    1490                1495                1500
Leu Phe Ile Tyr Ser Ser Lys Asp Leu Lys Asp Ile Arg Ile Ile Asn
1505                1510                1515                1520
Lys Gly Asp Val Lys Leu Leu Ile Gly Asn Tyr Phe Lys Asp Asp Met
                1525                1530                1535
```

```
Lys Val Ser Leu Ser Phe Thr Ile Glu Asp Thr Asn Thr Ile Lys Leu
            1540                1545                1550

Asn Gly Val Tyr Leu Asp Glu Asn Gly Val Ala Gln Ile Leu Lys Phe
        1555                1560                1565

Met Asn Asn Ala Lys Ser Ala Leu Asn Thr Ser Asn Ser Leu Met Asn
    1570                1575                1580

Phe Leu Glu Ser Ile Asn Ile Lys Asn Ile Phe Tyr Asn Asn Leu Asp
1585                1590                1595                1600

Pro Asn Ile Glu Phe Ile Leu Asp Thr Asn Phe Ile Ile Ser Gly Ser
            1605                1610                1615

Asn Ser Ile Gly Gln Phe Glu Leu Ile Cys Asp Lys Asp Lys Asn Ile
        1620                1625                1630

Gln Pro Tyr Phe Ile Asn Phe Lys Ile Lys Glu Thr Ser Tyr Thr Leu
    1635                1640                1645

Tyr Val Gly Asn Arg Gln Asn Leu Ile Val Glu Pro Ser Tyr His Leu
    1650                1655                1660

Asp Asp Ser Gly Asn Ile Ser Ser Thr Val Ile Asn Phe Ser Gln Lys
1665                1670                1675                1680

Tyr Leu Tyr Gly Ile Asp Arg Tyr Val Asn Lys Val Ile Ile Ala Pro
            1685                1690                1695

Asn Leu Tyr Thr Asp Glu Ile Asn Ile Thr Pro Val Tyr Lys Pro Asn
        1700                1705                1710

Tyr Ile Cys Pro Glu Val Ile Ile Leu Asp Ala Asn Tyr Ile Asn Glu
    1715                1720                1725

Lys Ile Asn Val Asn Ile Asn Asp Leu Ser Ile Arg Tyr Val Trp Asp
    1730                1735                1740

Asn Asp Gly Ser Asp Leu Ile Leu Ile Ala Asn Ser Glu Glu Asp Asn
1745                1750                1755                1760

Gln Pro Gln Val Lys Ile Arg Phe Val Asn Val Phe Lys Ser Asp Thr
            1765                1770                1775

Ala Ala Asp Lys Leu Ser Phe Asn Phe Ser Asp Lys Gln Asp Val Ser
        1780                1785                1790

Val Ser Lys Ile Ile Ser Thr Phe Ser Leu Ala Ala Tyr Ser Asp Gly
    1795                1800                1805

Phe Phe Asp Tyr Glu Phe Gly Leu Val Ser Leu Asp Asn Asp Tyr Phe
    1810                1815                1820

Tyr Ile Asn Ser Phe Gly Asn Met Val Ser Gly Leu Ile Tyr Ile Asn
1825                1830                1835                1840

Asp Ser Leu Tyr Tyr Phe Lys Pro Pro Lys Asn Asn Leu Ile Thr Gly
            1845                1850                1855

Phe Thr Thr Ile Asp Gly Asn Lys Tyr Tyr Phe Asp Pro Thr Lys Ser
        1860                1865                1870

Gly Ala Ala Ser Ile Gly Glu Ile Thr Ile Asp Gly Lys Asp Tyr Tyr
    1875                1880                1885

Phe Asn Lys Gln Gly Ile Leu Gln Val Gly Val Ile Asn Thr Ser Asp
    1890                1895                1900

Gly Leu Lys Tyr Phe Ala Pro Ala Gly Thr Leu Asp Glu Asn Leu Glu
1905                1910                1915                1920

Gly Glu Ser Val Asn Phe Ile Gly Lys Leu Asn Ile Asp Gly Lys Ile
            1925                1930                1935

Tyr Tyr Phe Glu Asp Asn Tyr Arg Ala Ala Val Glu Trp Lys Leu Leu
        1940                1945                1950
```

-continued

Asp Asp Glu Thr Tyr Tyr Phe Asn Pro Lys Thr Gly Glu Ala Leu Lys
            1955                1960                1965

Gly Leu His Gln Ile Gly Asp Asn Lys Tyr Tyr Phe Asp Asp Asn Gly
        1970                1975                1980

Ile Met Gln Thr Gly Phe Ile Thr Ile Asn Asp Lys Val Phe Tyr Phe
1985                1990                1995                2000

Asn Asn Asp Gly Val Met Gln Val Gly Tyr Ile Glu Val Asn Gly Lys
            2005                2010                2015

Tyr Phe Tyr Phe Gly Lys Asn Gly Glu Arg Gln Leu Gly Phe Phe Asn
        2020                2025                2030

Thr Pro Asp Gly Phe Lys Phe Gly Pro Lys Asp Asp Leu Gly
    2035                2040                2045

Thr Glu Glu Gly Glu Leu Thr Leu Tyr Asn Gly Ile Leu Asn Phe Asn
2050                2055                2060

Gly Lys Ile Tyr Phe Phe Asp Ile Ser Asn Thr Ala Val Val Gly Trp
        2065                2070                2075                2080

Gly Thr Leu Asp Asp Gly Ser Thr Tyr Tyr Phe Asp Asp Asn Arg Ala
            2085                2090                2095

Glu Ala Cys Ile Gly Leu Thr Val Ile Asn Asp Cys Lys Tyr Tyr Phe
            2100                2105                2110

Asp Asp Asn Gly Ile Arg Gln Leu Gly Phe Ile Thr Ile Asn Asp Asn
        2115                2120                2125

Ile Phe Tyr Phe Ser Glu Ser Gly Lys Ile Glu Leu Gly Tyr Gln Asn
        2130                2135                2140

Ile Asn Gly Asn Tyr Phe Tyr Ile Asp Glu Ser Gly Leu Val Leu Ile
2145                2150                2155                2160

Gly Val Phe Asp Thr Pro Asp Gly Tyr Lys Tyr Phe Ala Pro Leu Asn
            2165                2170                2175

Thr Val Asn Asp Asn Ile Tyr Gly Gln Ala Val Lys Tyr Ser Gly Leu
            2180                2185                2190

Val Arg Val Asn Glu Asp Val Tyr Tyr Phe Gly Glu Thr Tyr Lys Ile
        2195                2200                2205

Glu Thr Gly Trp Ile Glu Asn Glu Thr Asp Lys Tyr Tyr Phe Asp Pro
    2210                2215                2220

Glu Thr Lys Lys Ala Tyr Lys Gly Ile Asn Val Val Asp Asp Ile Lys
2225                2230                2235                2240

Tyr Tyr Phe Asp Glu Asn Gly Ile Met Arg Thr Gly Leu Ile Ser Phe
            2245                2250                2255

Glu Asn Asn Asn Tyr Tyr Phe Asn Glu Asp Gly Lys Met Gln Phe Gly
            2260                2265                2270

Tyr Leu Asn Ile Lys Asp Lys Met Phe Tyr Phe Gly Lys Asp Gly Lys
        2275                2280                2285

Met Gln Ile Gly Val Phe Asn Thr Pro Asp Gly Phe Lys Tyr Phe Ala
    2290                2295                2300

His Gln Asn Thr Leu Asp Glu Asn Phe Glu Gly Glu Ser Ile Asn Tyr
2305                2310                2315                2320

Thr Gly Trp Leu Asp Leu Asp Gly Lys Arg Tyr Tyr Phe Thr Asp Glu
            2325                2330                2335

Tyr Ile Ala Ala Thr Gly Ser Leu Thr Ile Asp Gly Tyr Asn Tyr Tyr
            2340                2345                2350

Phe Asp Pro Asp Thr Ala Glu Leu Val Val Ser Glu
        2355                2360

AGENTS USEFUL FOR INACTIVATION OF RAS SUBFAMILY PROTEINS

This is a Continuation of: International Appln. No. PCT/EP97/00426 filed Jan. 31, 1997 which designated the U.S.

The invention relates to methods of inactivation of p21 Ras, especially in its active oncogenic mutation, and agents therefor.

It is known that many diseases result from aberrations in signalling pathways. It is apparent that proto-oncogenes and oncogenes code for proteins which are involved in cell signalling and participate in the regulation of cell proliferation, cell division and cell death. Thus, growth factors, and their receptors, cellular thyrosine kinases, Ras proteins, adapter molecules, cyclines and transcription factors and their co-factor proteins play a pivotal role in cell proliferation. Activating mutations of such molecules disrupt the normal patterns of signalling and lead, in some case, to enhanced cell growth. Such an initial oncogenic mutation is, for example, the mutation glycine 12 to valine in the Ras proto-oncogene.

Further signal transduction molecules modified by our enzymic activity are Rac of the Rho subfamily, Rap and Ral of the Ras subfamily of small GTP-binding proteins.

Oncogenic mutation in Ras occurs in 40% of all cancer, and over 85% of certain cancers, such as pancreatic cancer and colon cancer. The oncogenic form of Ras continues to be involved even at the advanced stages of colon cancer, although in many instances, it is the first oncogenic mutation which occurs in the colon tissue (Shirasawa et al., Science 260 (1993) 85–88). The Ras proto-oncoproteins are activated by upstream mitogenic signals such as receptor thyrosine kinase and mitogenic peptides which act via the serpentine receptor GTP-binding protein signal-transduction system. Therefore, Ras is a transducer of upstream mitogenic signals, and an oncoprotein, when mutated. Thus, inhibition of Ras function is a prime target for cancer therapy.

Inhibition of Ras function can be obtained by inhibition of Ras farnesylation. The enzyme farnesyl protein transferase catalyzes the farnesylation of Ras by farnesyl pyrophosphate. Such inhibitors are described, for example, by Kohl, N. E., et al., Science 260 (1993) 1934–1937. It is further discussed to inhibit Ras activation by gribstatins or sostatins (Razakis-Adocke, M., et al., Nature 363 (1993) 83–85; Segal, M., et al., Proc. Natl. Acad. Sci. USA 90 (1993) 5564–5568). It is further proposed to inhibit Ras/Raf-1 interaction (Levitzky, A., Euro. J. Biochem. 226 (1994) 1–13). The efficiency of the inhibition of the Ras pathway by the known substances is not yet satisfactory however.

The Ras inhibitors which are known are non-peptidic substances. For cell-specific targeting, however, preferably, fusion proteins, in particular, immunotoxins, are used, which can be prepared chemically or by genetic engineering techniques. However, no toxin is known which specifically inhibits active Ras oncoproteins in mammalian, especially human, cells.

Several different species of the genus Clostridium produce large molecular weight (250–300 kDa) cytotoxins which cause effects on the actin cytoskeleton, including disruption of actin stress fibers and rounding up of cell bodies. This sub-group of clostridial cytotoxins includes toxins A and B from *Clostridium difficile*, lethal toxin (LT) (SEQ ID NO:6, see Green et al., Gene, 161:57–61, 1995) and hemorragic toxin (HT) from *Clostridium sordellii* and *Clostridium novyi* α-toxin (Bette, P., et al., Toxicon 29(1991) 877–887). Enterotoxin A and cytotoxin B have been characterized by Sullivan, N. M. et al., Infect. Immun. 35 (1982) 1032–1040, von Eichel-Streiber, C., et al., Microbiol. Pathogenesis 2 (1987) 307–318. Toxin A and toxin B are glucosyltransferases which modify threonine 37 of the GTPase Rho. By attracting of glucose at this position of Rho, this GTPase is blocked in its function. Recently, toxin B and toxin A from *C. difficile*, the causative agent of antibiotic-associated diarrhea (Lyerly, D. M., et al., Clin. Microbiol. Rev. 1 (1988) 1–18), were shown to covalently modify the mammalian protein Rho by UDP-Glc dependent glucosylation of threonine 37 (Just, I. et al., Nature 375 (1995) 500–503; Just, I., et al., J. Biol. Chem. 270 (1995) 13932–12936). Rho is a small ras related GTP-binding protein involved in the control of actin polymerization (Hall, A., Ann. Rev. Cell Biol. 10(1994) 31–34). Glucosylation of threonine 37 of Rho by *C. difficile* toxins A or B apparently inactivates this protein and results in a loss of actin stress-fiber assembly.

*C. sordellii* produces two toxins; LT and HT, two major virulence factors inducing gas gangrene and hemorragic diarrhea in humans and animals (Arseculeratne, S. N., et al., J. Med. Microbiol. 2 (1969) 37–53). These *C. sordellii* toxins have some similarities with the toxins A and B of *C. difficile* in terms of amino-acid sequences and immunological epitopes (Martinez, R. D., and Wilkins, T. D., J. Med. Microbiol. 36 (1992) 30–32). Despite these similarities, it seems that LT and toxins A or B affect different intracellular target proteins. LT causes morphological and cytoskeletal effects different from those elicited by the *C. difficile* toxins. The effects consist in the rounding of cell bodies with the reorganization of F-actin structures into numerous cell surface filopodia and a loss of actin stress-fibers (Popoff, M. R., Infect. Immun. 55 (1987) 3543; Giry, M., et al., Infect. Immun. 63 (1995) 4063–4071). In addition, it was shown that overexpression of Rho A, B or C cDNAs in HeLa cells protects these cells from the effects of toxin A and B but not from that of LT (Giry, M., et al., Infect. Immun. 63 (1995) 4063–4071). These observations clearly pointed out that Rho small GTP-binding proteins were the main substrate for the *C. difficile* toxins.

Toxins A and B from *C. difficile* have been shown to covalently modify and thereby inactivate the small GTP-binding protein Rho resulting in the disruption of F-actin structures (Just, I., et al., J. Biol. Chem. 269 (1994) 10706–10712; Just, I., et al., J. Clin. Invest. 95 (1995) 1026–1031). "In vitro" and "in vivo" evidence indicates that toxins A and B modify Rho A by UDP-Gic dependent glucosylation of threonine 37 (Just, I., et al., Nature 375 (1995) 500–503; Just, I., et al., J. Biol. Chem. 270 (1995) 13932–13936). In addition to Rho A toxins A and B of *C. difficile* also "in vitro" modify Rac1 and Cdc42 (Just, I., et al., Nature 375 (1995) 500–503; Just, I., et al., J. Biol. Chem. 270 (1995) 13932–13936), two other proteins of the Rho sub-family involved in the control of membrane ruffling and filopodia formation respectively (Ridley, A. J., et al., Cell 70 (1992) 401410; Nobes, C. D., and Hall, A, Cell 81 (1995) 53–62). Also, it has recently been reported that the c toxin from *C. novyi* is a glucosyl-transferase which acts on the cytoskeleton through modification of Rho. However, in this case, UDP-Glc was not the cofactor required for modification.

M. R. Popoff, in Infect. Immun. 55 (1987) 3543, describes a purification protocol for *C. sordellii* lethal toxin (LT) as well as phenomenology of LT action. Popoff does not state anything about the molecular targets or the enzymatic action of LT.

G. A. Green et al., in Gene 161 (1995) 5761, describe the cloning and sequencing of the LT encoding gene of strain 6018. The authors do not present any clue towards the mode of action of LT.

C. v. Eichel-Streiber, in Mol. Microbiol. 17 (1995) 313–321, provides data which indicate that some *C. difficile* toxins behave like *C sordellii* LT. ToxB-1470 induces morphological effects identical to those of LT, but both clearly different from those of ToxB. The sequence of tcdB-1470 is presented and a comparison of tcdB of *C difficile* strain VPI10463 is shown that narrows down the catalytic domain of the toxins to approximately the 900 amino acids from the amino-terminus on.

WO 94/22476 describes the use of Sapronin as an adjuvant in preparing a multivalent vaccine against bacteria and toxins of the genus Clostridia. *C. sordellii* is one of the strains the described immunization is addressed to. Strain and/or toxin are used as antigens for inducing protection in animals after different routes of innoculation.

SUMMARY OF THE INVENTION

The invention provides a method for the inhibition of p21 Ras by a polypeptide with glucosylation activity of lethal toxin (LT) from *Clostridium sordellii*. It was, surprisingly, found that LT inactivates Ras by glucosylation of Ras subfamily proteins, preferably by glucosylation of Ras threonine 35. This was completely unexpected because the toxins A and B, which are, in regard to their sequence, largely homologous to LT, inactivate small G-proteins of only the Rho subfamily.

An object of the invention, therefore, is a method of treating a patient with a disorder, characterized by an activating mutation in the Ras proto-oncogene, comprising contacting cells, preferably, specifically tumor cells, of said patient with a protein having the toxic activity of *Clostridium sordellii* toxin LT under conditions favoring inactivating of Ras by glucosylation of threonine 35 in said cell. Such a disorder is, preferably, cancer, more preferably, pancreas or colon cancer.

A further object of the invention is an immunotoxin with the glucosylating activity of toxin LT, whereby Ras is inactivated by glucosylation of Ras' threonine 35.

A further object of the invention is a method wherein said immunotoxin contains a first part, a second part, and a third part, connected by covalent bonds:

(i) the first part including a target cell specific binding domain, which domain is able to cause the immunotoxin to bind to said patient's cell;
(ii) the second part including a translocation domain of a protein, which domain is capable of translocating the third part across the cytoplasmic membrane of the cell, and
(iii) the third part including a polypeptide with the toxic activity of the catalytic domain of toxin LT from *Clostridium sordellii* LT.

Such an immunotoxin preferably contains, as the target cell, a specific binding domain, the antibody or active fragment thereof.

A further object of the invention is a composition useful in treating a pathological condition, characterized by an activating mutation in the Ras proto-oncogene, comprising an immunotoxin which contains a first part, a second part, and a third part, connected by covalent bonds:

(i) the first part including a target cell specific binding domain, which domain is able to cause the immunotoxin to bind to said patient's cell;
(ii) the second part including a translocation domain of a protein, which domain is capable of translocating the third part across the cytoplasmic membrane of the cell, and
(iii) the third part including a polypeptide with the toxic activity of the catalytic domain of toxin LT from *Clostridium sordellii* LT, and a pharmaceutically acceptable carrier.

A further object of the invention is the afore-mentioned immunotoxin, wherein the first part preferably is an antibody or an active fragment thereof.

A further object of the invention is an immunotoxin with the glucosylating activity of toxin LT on Ras.

A further object of the invention is a method of manufacturing a therapeutic agent, characterized by combining a therapeutically useful amount of an immunotoxin according to the invention with a therapeutically acceptable adjuvant or carrier.

DETAILED DESCRIPTION OF THE INVENTION

It was found that LT, like toxins A and B of *C. difficile*, is also a glucosyltransferase using UDP-Glc to modify small GTP-binding proteins. Surprisingly, LT "in vitro" glucosylates Ras, Rap2, Ral and Rac1. The Ral modification is not seen if a GST-fusion protein is used as target molecule (compare FIGS. 3A and 3B). LT had no effect on Rho, nor on Cdc 42, two of the main substrates for *C. difficile* A and B toxins.

The effects induced by LT on the HeLa cell actin cytoskeleton are obviously different from those elicited by toxins A and B of *C. difficile*. The LT effects consist in the disruption of actin-stress-fibers and the formation of filopodia containing F-actin and fimbrin/plastin (Giry, M., et al., Infect. Immun. 63 (1995) 4063–4071). Glucosyltransferase activity of both *C. difficile* and *C. novyi* toxins is directed towards GTP-binding proteins of the Rho-subfamily. *C. sordellii* LT is the first toxin which mainly acts on the Ras-subfamily of GTPases. The specific effect of LT on the HeLa cell actin cytoskeleton is fundamentally different to what is observed with Tox A or B of *C. difficile* (Giry, M., et al., Infect. Immun. 63 (1995) 4063–4071). Since both Tox B (or A) and LT are able to glucosylate Rac (Just, I., et al., Nature 375 (1995) 500–503; Just, I., et al., J. Biol. Chem. 270 (1995) 13932–13936), the specific activity of LT on the cytoskeleton cannot be attributed to Rac modification alone. It seems that the combination of the modified GTPases causes LT to induce its cytopathogenic effect. Thus, Rap and Ral modification by LT could be a key event for LT actin cytoskeleton activity.

LT inactivates Ras by glucosylation of threonine 35 which corresponds to threonine 37 of Rho (Madaule, P., and Axel, R., Cell 41 (1985) 31–40), the residue modified by toxins A and B (Just, I., et al., Nature 375 (1995) 500–503; Just, I., et al., J. Biol. Chem. 270 (1995) 13932–13936). LT acts in the cytosol and "in vivo" glucosylates small Mr 21 kDa molecules resulting in the inactivation of Ras, since serum-starved Swiss 3T3 cells intoxicated with LT have no Ras-dependent induced MAP-kinase phosphorylation (see FIG. 5).

It seems reasonable that amino acid sequences apart from the threonine 35 acceptor site of glucosylation enable LT to specifically recognize the various small G-proteins.

LT-glucosylation of Ras on threonine 35 induced a small but significant decrease in the $K_{off}$ of GDP, most likely due to a higher affinity of the glucosylated Ras for magnesium.

Such a difference in magnesium affinity has not been observed for the threonine 35 alanine ($^{[T35A]}$) mutant of Ras (John, J., et al., J. Biol. Chem. 268 (1993) 923–929). Apart from this small difference, the T35 glucosylated form of Ras in the GTP-bound form has properties very similar to those of the $^{[T35A]}$ mutant: a 4 fold increase in the GTP $K_{off}$ and a 4 to 5 times slower rate of GTP hydrolysis (John, J., et al., J. Biol. Chem. 268 (1993) 923–929). It therefore seems that the T35 glucosylation of Ras, as the $^{[T35A]}$ mutant of Ras, has a much decreased affinity for the Raf Ras-binding domain (RBD) (Herrmann, C., et al., J. Biol. Chem. 270 (1995) 2901–2905). The $^{[T35A]}$ mutant of Ras has a 200 fold reduced affinity for Raf-RBD (Herrmann, C., et al., J. Biol. Chem. 270 (1995) 2901–2905) and represents the mutation that has the most drastic effect on Ras-RBD interaction (Herrmann, C., et al., J. Biol. Chem. 270 (1995) 2901–2905). Threonine 35 contacts both magnesium and γ-phosphate in the GTP-bound form, and a water molecule which also makes a hydrogen bound with aspartic acid 38 in the Rap/Raf-RBD complex (Nassar, N., et al., Nature 375 (1995) 554–560). Threonine 35 is conserved in all of the small G-proteins and is an essential residue of the switch I region (Pai, E. F., et al., EMBO J. 9 (1990) 2351–2359). Thus the modification of threonine 35 either by mutation [T35A] or by glucosylation would result in the inability of Ras to interact with its effector (Pai, E. F., et al., EMBO J. 9 (1990) 2351–2359). Even the conservative threonine 35 serine mutation greatly decreases (about 20 fold) the transforming potential of an oncogenic Ras, pointing to the importance of this residue in switching to the active conformation and/or interacting with the Raf effector (White, M. A., et al., Cell 80 (1995) 533–541).

Taking into account that LT is the first toxin which inactivates the Ras small GTP-binding protein, it is a powerful laboratory reagent to explore cellular signalling pathways stimulated by this molecule and a useful therapeutic agent for inhibiting Ras activity in vivo. Toxin LT is organized like many other bacterial toxins, especially like *C. difficile* toxins A and B (von Eichel-Streiber, C., et al., Mol. Microbiol. 17 (1995) 313–321; von Eichel-Streiber, C., et al., Trends in Microbiology 4 (October 1996) 375–382) or *P. aeruginosa* exotoxin A, and all clostridial neurotoxins (Choe, S., et al., Nature 357 (1992) 216–222; Allured, V. S., et al., Proc. Natl. Acad. Sci. USA 83 (1986) 1320–1324; Prior, T. I., et al., Biochemistry 31 (1992) 3555–3559; Montecucco, C., and Schiava, G., Trends Biochem. Sci. 18 (1993) 324–326). Especially toxin LT is organized as a single-chained toxin consisting of three domains: The N-terminal domain constitutes the catalytic domain, followed by the intermediary translocation domain, and the final C-terminal region contributing to cellular binding. The DNA and protein sequence of toxin LT are described in Green, G. A., et al., Gene 161 (1995) 57–61, and EMBL DataBank Access No. X82638. The catalytic domain of the toxin consists of approximately the first 1020 amino acids of the sequence or parts thereof which have the glucosyltransferase activity of LT.

An immunotoxin according to the invention is a multidomain protein containing a first part, a second part and a third part usually connected by covalent bonds:

1. the first part including a target cell specific binding domain of a cell binding ligand, which domain is able to cause the immunotoxin to bind to a target mammalian, especially human, cell;
2. the second part including a translocation domain of a protein, which domain is capable of translocating the third part across the cytoplasmic membrane of the cell, and
3. the third part including a polypeptide with the activity of the toxin domain (the catalytic domain) of toxin LT.

The hybrid molecule is produced by expression of a recombinant DNA molecule encoding the multidomain protein molecule or by chemical linkage between the domains (see e.g. Monoclonal Antibodies in Clinical Medicine, ed. McMichael, A. J., and Fabre, J. W., Academic Press, London (1982) 168–192).

The first part is a moiety which binds specifically to the target cells. Therefore, as the first part there is used a binding partner for a surface receptor or marker which is highly expressed on tumor cells and has a high degree of selectivity for tumor cells. The receptor for the binding partner is a surface molecule on the target cells which is expressed in considerably higher amounts and to a larger extent on the target cells than on normal cells. Examples for such suitable binding partners are antibodies, cytokines, melanoma stimulating hormone (MSH), other hormones or growth factors.

The target cell-specific binding domain recognizing a cell surface structure, such as a receptor protein or a surface antigen on the target cell, is e.g. derivable from a ligand of a cell specific receptor, such as a Fc receptor, transferrin receptor, EGF receptor, asialoglycoprotein receptor, cytokine receptor, such as a lymphokine receptor, a T cell specific receptor, e.g. CD 45, CD4 or CD8, the CD 3 receptor complex, TNF receptor, CD 25, erbB-2, an adhesion molecule, such as NCAM or ICAM, and mucine. Suitable ligands include antibodies specific for said receptor or antigen. Further molecules suitable as ligand domain in the multidomain protein of the invention include factors and growth factors, e.g tumor necrosis factor, e.g. TNF-α, human growth factor, epidermal growth factor (EGF), platelet-derived growth factor (PDGF), transforming growth factor (TGF), such as TGFα or TGFβ, nerve growth factor, insulin-like growth factor, a peptide hormone, e.g. glucagon, growth hormone, prolactin, or thyroid hormone, a cytokine, such as interleukin, e.g. IL-2 or IL-4, interferon, e.g. IFN-γ, or fragments or mutants of such proteins with the provision that such fragments and mutants fulfill the above requirements for a ligand domain. For example, suitable antibody fragments include Fab fragments, Fv constructs, e.g. single chain Fv contructs (scFv) or an Fv construct involving a disulfide bridge, and the heavy chain variable domain. The ligand domain may be of natural or synthetic origin and will vary with the particular type of target cell.

Further B lymphocyte specific MAbs which are useful binding partners are the pan-B MAbs, such as anti-CD20, CD21, CD22 or anti-CD37. These MAbs, labeled with high doses of $^{131}I$, have been used with some success for B cell lymphoma therapy (Press, O. W., et al., J. Clin. Onc. 7 (1989) 1027–1038; Goldenberg, et al., J. Clin. Oncology 9 (1991) 548–568; Kaminski, et al., New England Journal of Medicine 329 (1993) 459–465; Press, et al., New England Journal of Medicine 329 (1993) 1219–1224).

For the treatment of T cell lymphomas, MAbs specific for either the idiotype or the α or β chain of the T cell receptor (TCR) are useful in the conjugates according to the invention. Some of these anti-α or β chain MAbs from TCR were first described as anti-T cell idiotypes (Reinherz, E. L., et al., Immunol. Rev. 74 (1983) 83–112; Carrel, S., et al., Eur.J Immunol., 16 (1986) 649–652) but were subsequently found to be shared by 1 to 10% of normal T lymphocytes.

Glioblastoma cells also show various degrees of expression of class II MHC which can be enhanced by interferon-γ. A certain percentage (40 to 60%) of glioma express a high density of the EGF receptor, which could be a good target for the conjugates (Kalofonos, H. P., et al., J. Nucl. Med. 30 (1989) 1636–1645; Humphrey, P. A., et al., Proc. Natl. Acad. Sci. USA 87 (1990) 4207–4211), especially if the conjugates are injected locally in cystic tumors or after surgical removal of the major part of the tumor. In the case of an intracraneal injection of the conjugates it is preferred to inject also locally autologous peripheral blood lymphocytes containing effector T cells capable of recognizing the tumor cells with immunogenic peptides on their surface associated with MHC.

Carcinoma cells rarely express class II MHC. Thus, it is preferred to use the class I processing pathway in order to apply a therapy to these tumors. Several MAbs with different degrees of selectivity for carcinoma cells have been described. Some of them, such as those reacting with the Erb-B2 receptor (Harwerth I.-M., et al., J. Biol. Chem. 21 (1992) 15160–15167; Batra, J. K., et al., Proc. Natl. Acad. Sci. USA 89 (1992) 5867–5871; Kasprzyk, P. G., et al, Cancer Res. 52 (1992) 2771–2776; Wels, W., et al., Cancer Res. 52 (1992) 6310–6317) and/or the EGF receptor (Atlas, I., et al., Cancer Res. 52 (1992) 3335–3339) or MAb A33 from the group of Old (Welt, S., et al., J. Clin. Oncol. 8 (1990) 1894–1906), are readily internalized by carcinoma cells and could be used in the method according to the invention.

The second part is a "translocation domain". "Translocation" means the facilitation of movement of the catalytic domain (in the case of LT: glucosyltransferase) from the exterior surface of a cellular membrane (or what constituted the exterior surface prior to formation of an endocytic vesicle) through the membrane and into the cytosol at the interior of the cell. This domain is therefore a segment of a protein which, when the protein is bound to the exterior surface of a cellular membrane, is capable of translocating some portion of that protein through the membrane. As translocation domain it is preferred to use the translocation domain of a naturally occurring toxin (e.g. diphtheria toxin or Pseudomonas exotoxin or toxin LT). The translocation domain of diphtheria toxin consists, for example, essentially of amino acids $Ser^{194}$ to $Ser^{535}$.

A further object of the invention is a vector, especially a retroviral or non-viral vector, which interacts with tumor cells and carries the catalytic principle of toxin LT. Said vector contains a nucleotide acid fragment which codes for the first 1020 amino acids of toxin LT or parts thereof which have the toxic activity of the catalytic domain of LT.

The third part of the multidomain protein according to the invention is the catalytic domain. Toxin LT can be isolated according to Popoff, M. R., Infect. Immun. 55 (1987) 35–43, or modified according to von Eichel-Streiber, C., et al., Microbiol. Pathogenesis 2 (1987) 307–318. Its sequence is described by Green, G. A., et al., Gene 161 (1995) 57–61. The toxin domain consists of approximately the first 1000 amino acids of this sequence. In the multidomain protein according to the invention, the length of the toxin domain can vary as long as the toxic activity remains essentially unchanged.

In a preferred embodiment, the second and the third part of the multidomain protein result from toxin LT. Therefore, the protein contains the translocation domain and the catalytic domain of LT. Thus, this combined second and third parts comprise approximately the first amino acids 1–1020 and 1021–1700 of the LT sequence (from the N-terminus on).

Immunotoxins according to the invention can be produced by either of two principally different methods:

In one method, an antibody or a fragment thereof (normally generated proteolytically, e.g. Fab-fragment) is chemically coupled in vitro to a toxin or toxin fragment. For practical reasons, the antibody part in this type of immunotoxin is either a complete antibody (consisting of two light and two heavy chains) or, more preferably, a Fab-fragment (consisting of one light chain and the VH- and CH1-regions of the heavy chain). The chemical coupling of the toxin part to the antibody part will not normally lead to a completely defined, homogeneous immunotoxin molecule, as surface residues in different positions may participate. In addition, the ratio of antibody to toxin will vary to a certain degree.

In the other method, the immunotoxin is generated by recombinant DNA techniques, which leads in any case to a defined, homogeneous molecule. The size of the antibody part should be as small as possible to obtain a small immunotoxin with good tissue penetration. In this method, the smallest practically available antibody fragment is not the Fab-fragment, but the functional variable domain of an antibody, consisting of the VH-region of the heavy chain and the VL-region of the light chain only. VH- and VL-region (polypeptide chains each of about 100 amino acids) have to form a functional assembly, the variable domain, which confers antigen binding. In the absence of any of the remaining parts of an antibody, VH- and VL-region form very labile complexes only. Therefore, their complex is preferably stabilized by covalent bonds.

One possibility is to fuse on the DNA level VH-region, VL-region (or vice versa) and the toxin part. Upon expression, a single polypeptide chain is formed, wherein VH- and VL-region, being connected by a peptide linker, fold into a stable variable domain, while the toxin is fused e.g. to VL via a second peptide linker (see Brinkmann et al. 1992, PNAS 89, 3075–3079). The length of both peptide linkers is variable and may in some instances even be reduced to a single peptide bond. A molecule of this type has been termed a "single chain immunotoxin", analogous to the term "single chain antibody" or scFV, which is used for a single polypeptide chain containing both VH and VL connected by a peptide linker or bond.

Another possibility to stabilize the VH- and VL-assembly is described in Brinkmann et al. 1993 (PNAS 90, 7538–7542). In this technique, amino acids on VH and VL were defined by computer aided modelling, which are closely adjacent in the VH-VL-complex. The naturally occurring amino acids in these positions were then on the DNA level replaced by a cystein each. To obtain a functional immunotoxin in this case, two separate polypeptide chains are expressed (in separate E. coli cells), one being the VH-region only, the other the VL-region fused by a peptide linker to the toxin part. These two polyeptide chains are mixed under appropriate conditions and thus assemble into a functional immunotoxin, where VH and VL in the variable antibody domain are connected by a disulfide bond between the two cysteins introduced by genetic engineering. The antibody part of this type of immunotoxin has been designated dsFV and the whole molecule consequently as "dsFV-immunotoxin".

Of course, there exist additional possibilities to produce immunotoxins by recombinant DNA techniques, for instance by using the larger Fab-fragment (VH-CH1 non-covalently assembled to VL-CL, while one of them is fused by a peptide linker to the toxin). However, the possibilities described by Brinkmann et al. 1992 and Brinkmann et al. 1993 are to be preferred.

An immunotoxin is produced preferably as a single polypeptide chain in E. coli. The polypeptide is obtained in an inactive form and has to be activated by in vitro renaturation.

In another method, an immunotoxin is produced as two polypeptide chains in two separate E. coli strains. Both polypeptides are obtained in an inactive form. They are mixed in equimolar amounts and activated by in vitro renaturation. During this process, both polypeptides assemble to the active heterodimeric immunotoxin.

Such immunotoxins and methods of producing same are described, for example, in EP-B 0 194 276, WO 88/01649, U.S. Pat. No. 4,947,778, WO 88/09344, U.S. Pat. No. 5,132,405 and U.S. Pat. No. 5,091,513

A further object of the invention is a retroviral or non-viral vector which contains a nucleic acid fragment which codes at least for a translocation domain and the catalytic domain of LT. Such a vector can be used as a gene therapeutic agent for transfection of tumor cells of a patient. There is preferably used a retroviral or non-viral vector utilizable for transformation of tumor cells, which mediates expression of the aminoterminal 1020 amino acids, or a fragment thereof with preserved glucosyltransferase activity. This vector can be used in an in vivo or ex vivo gene therapy.

Within the multidomain protein of the invention the translocation domain functions to enhance the transfer of the catalytic domain through the cellular or endosomal membrane into the cytosome. WO 94/04696 describes a nucleic acid transfer system wherein, as a translocation domain and a receptor binding domain, the cognate domains of P. exotoxin A are used. However, the transfection efficiency and specificity of such transfer systems are very low. The invention, therefore, provides an improved nucleic acid transfer system exhibiting a high transfection efficiency and specificity. Suitable translocation domains are derivable from toxins, particularly bacterial toxins, such as *C. difficile* toxin A or B, *C. sordellii* toxin LT, exotoxin A, Colicin A, d-endotoxin, diphtheria toxin, *Bacillus anthrox* toxin, Cholera toxin, Pertussis toxin, *E. coli* toxins, Shigatoxin or a Shiga-like toxin. The translocation domain does not include that part of the parent toxin molecule which confers the toxic effect of the molecule, except when the partent toxin is toxin LT. Advantageously, the translocation domain of the recombinant protein of the invention is derivable or essentially derivable from that very part of the parent toxin which mediates internalization of the toxin into the cell, e.g. amino acids 193 or 196 to 378 or 384 of diphtheria toxin.

The following examples, references, sequence listing and drawing are, provided to aid the understanding of the present invention, the true scope of which is set forth in the appended claims. It is understood that modifications can be made in the procedures set forth without departing from the spirit of the invention.

| Sequence Listing | |
|---|---|
| SEQ ID NO:1 | Primer BCS1C (bases 465–495 of the total sequence (EMBL Data-Bank Accession No. X82638). |
| SEQ ID NO:2 | Primer BCD2N (complementary to bases 3528–3556 of the total sequence) |
| SEQ ID NO:3 | Primer BCD2C (bases 3528–3556 of the total sequence) |
| SEQ ID NO:4 | Primer BCS3N (complementary to bases 5552–5579 of the total sequence) |

FIGURE LEGENDS

FIG. 1: LT induced Glucosylation of $M_r$ 21 kDa proteins in HeLa cell lysates: HeLa cell lysates were incubated with UDP-[$^{14}$C] Glc in the absence (lane A) or presence (B-D) of LT. Specificity of UDP-Glc labelling by LT was tested by incubating Hela lysates with a 10 fold excess of unlabeled UDP-Glc (C) or UDP-glucuronic acid (D)) together with UDP-[$^{14}$C] Glc. $M_r$ are in kiloDalton.

FIG. 2: "In vivo" glucosylation of cellular Mr 21 kDa proteins in Rat fibroblasts by LT: Rat-1-EI-Rap2.31.A8 fibroblasts were incubated with the indicated concentrations of LT for 120 min detached from the culture dishes, lysed and glucosylated by LT with UDP-[$^{14}$C] Glc as described in the Methods section. Lane A; shows labelling of Mr 21 kDa proteins in cells not incubated with LT "in vivo" prior to the radioactive "in vitro" LT glucosylation of the cell lysate. B, C, D and E; show labelling of Mr 21 kDa proteins in cells incubated first "in vivo" with respectively 5, 0.5, 0.05, and 0.005 mg/ml of LT prior to the radioactive "in vitro" LT glucosylation of the cell lysates FIG. 3A: Glucosylation of recombinant Ras-related GTPases by LT: H-Ras, Rap2, Rac1, Cdc42, RhoA, Rab6, Ral-GST and Rac-GST (ca 1 mg/assay) were incubated with LT and UDP-[$^{14}$C] Glc. Panel A; Phosphorimage.B; Coomassie staining of the gel. $M_r$ are in kiloDalton.

FIG. 3B: Autoradiogram of the glucosylation of the Ral-GTPase by the following clostridial cytotoxins: lanes 1 and 2, *C. difficile* strain-10463 towns: 1: TcdA, 2: TcdB; lanes 3 and 4, *C. difficile* strain-1470 toxins: 3: TcdA; 4: TcdB; lane 5: glucosylation of Ral by LT prepared from *C. sordellii* IP-82; lane 6: Ral-modification by TcdB of *C. difficile* strain-8864.

FIG. 4: Localization of the LT catalyzed ($^{14}$C) glycosylation in H-Ras by microsequencing: Panel 4-1A; Separation by HPLC of the peptides generated by trypsin and radioactivity of each fraction (on 15 ml aliquot). Panels 4-2B and 4-2C; Purification by HPLC of fractions 39 and 40. Radioactivity associated with each peptide was counted on 50 ml aliquots. Panel 4-1D; Radioactivity associated with each Edman degradation cycle (each Edman cycle of peptide E and peptide D were combined and counted).

FIG. 5: EGF-induced mobility shift of MAP-kinases in cells pretreated with LT:. Serum starved Swiss 3T3 cells were treated with EGF and LT as shown in the figure. Cells were lysed and about 30 mg of total protein per experiment were electrophoreses and blotted and stained with the monoclonal antibody MK12. (ERK1: 44 kDa; ERK2: 42 kDa).

FIGS. 6A to 6H: Intracellular modulation of LT-action: A and B; phase contrast micrographs of Don-wt cells: A, typical cytopathogenic effect observed after treatment with LT (1.25 μg/ml; 3 h) in the presence of pre-immune serum (1/200 dilution). B, neutralisation of the cytopathogenic effect by adding rabbit anti-LT antibodies (dilution 1/200) to the medium containing LT (1.25 μg/ml; 3 h). C-H; microinjection experiments of Don-wt (C, D, G, H) or Don-Q (E, F) cells. C, E, G, fluorescence micrographs of D, F, H, (phase contrast micrographs) respectively. Big arrowheads point to cells microinjected, small arrowheads to cells solely treated with substances added to the medium. Fluorescein-staining was due to FITC-dextran added to the injected medium. C and D; typical rounding of Don-wt cells microinjected with LT (concentration in the micropipette 200 μg/ml) in a medium containing LT antibodies (dilution 1/200) to protect against any LT molecules possibly leaking out from injected cells. E and F; typical rounding of UDP-Glc deficient Don-Q cells exposed to LT (1.25 μg/ml; 3 h) in the medium, and then microinjected with UDP-Glc (concentration in the micropipette 100 mM). G and H; protection from rounding of Don-wt cells microinjected with neutralising anti-LT antibodies (serum diluted 1/10) and exposed to LT (1.25 µg/ml; 3 h) in the medium. The toxin is accessible to neutralising anti-LT antibodies once it reaches the cytosol.

Figure 7:
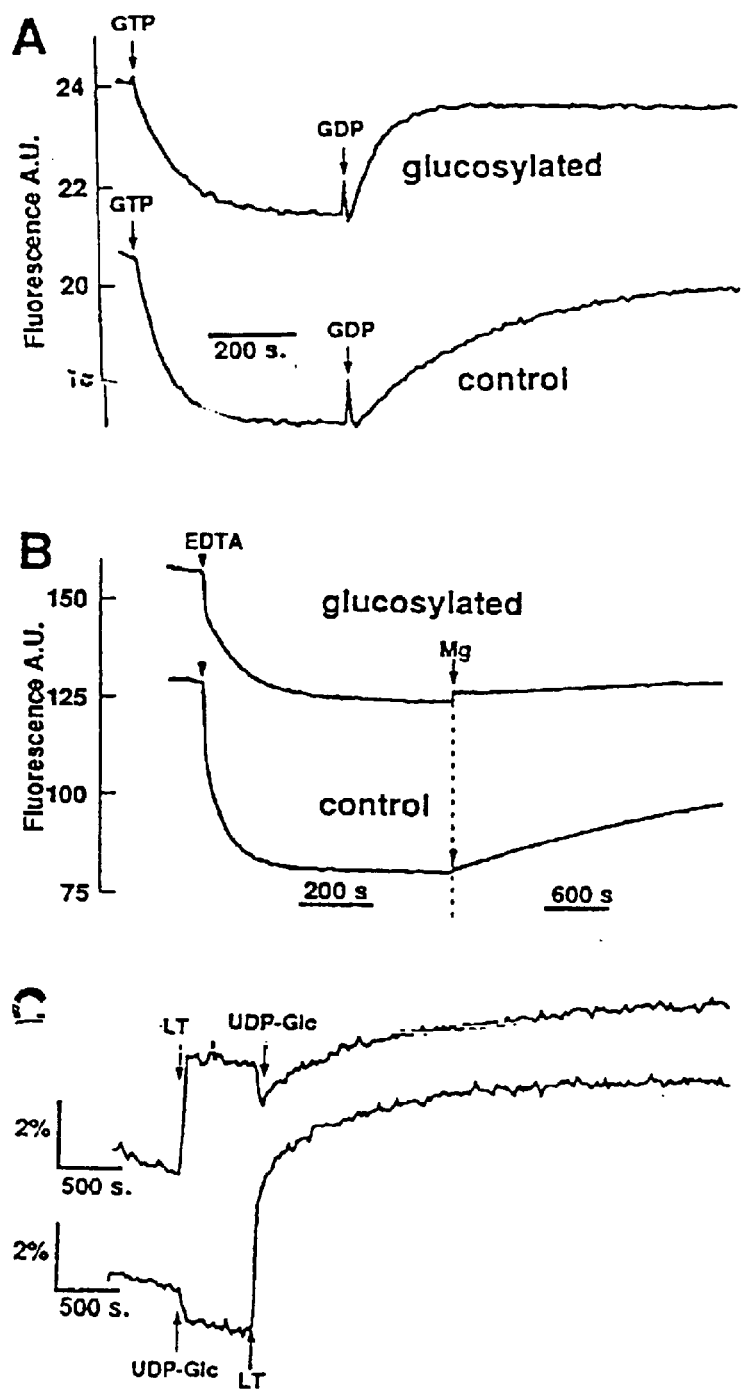

FIGS. 7A to 7C: Effect of LT catalysed glucosylation on nucleotide dissociation, GTPase activity and intrinsic fluorescence of $[Y64W]$Ras: FIG. 7A; GDP and GTP dissociation at low magnesium. Glucosylated or unmodified $[Y64W]$ Ras-GDP (0.5 µM) was activated, in the presence of 0.8 µM free magnesium (1 mM $MgCl_2$ and 2 mM EDTA), by the addition of 10 µM GTP (first arrow) deactivation was achieved by the addition of 500 µM GDP while its intrinsic fluorescence at 340 nm was continuously monitored. GDP dissociation rate constant: glucosylated: 0.0125 $s^{-1}$; control; 0017 $s^{-1}$. GTP dissociation rate constant: glucosylated 0.0125 $s_{-1}$; control: 0.0033 $s^{-1}$. FIG. 7B; GTP Hydrolysis at 1 mM magnesium. Glucosylated or unmodified $[Y64W]$Ras-GDP (0.5 µM) were incubated with 10 µM GTP in the presence of 1 mM magnesium. GDP/GTP exchange was initiated by the addition of 2 mM EDTA After 6 minutes, GT? hydrolysis was initiated by the addition of 2 mM $MgCl_2$ (1 mM free magnesium). Note the change in time scale after magnesium addition. FIG. 7C; Glucosylation of $[Y64W]$Ras-GDP induces a small increase in the intrinsic fluorescence of the protein. The fluorescence of $[Y64W]$Ras-GDP was continuously monitored while 0.8 µg/ml and 100 µM UDP-Glc were sequentially added to the fluorescence cuvette. In FIGS. 7A and 7C, the sample was excitated at 300 nm to minimize light absorption due to the large amount of nucleotides used in these experiments. In panel B, the excitation was set at 292 nm.

EXAMPLES

1. Materials

C. sordellii LT toxin was obtained from culture supernatants of the pathogenic *C. sordellii* IP82 strain and purified to homogeneity as previously described (Popoff, M. R., Infect. Immun. 55 (1987) 3543). Recombinant H-Ras, RhoA, Rac1, Rap2, Ral, Rab6 and Cdc42 proteins were made either in baculovirus (Rac1, Rab6 and Arf1) or in *E. coli* through either GST-fusions (H-Ras, Rap1, Ral, RhoA and Rac1) or a Histidine-tagged fusion (His-Cdc 42). The monoclonal antibody MK12 (Zymed, Cal.) was used for immunoblotting MAP kinases. The recombinant tyrosine 64 tryptophan ([$^{Y64W}$]) Ras mutant used for tryptophan fluorescencce experiments was produced in *E. coli* and purified as previously described (Antonny, B., et al., Biochemistry 30 (1991) 8287–8295).

2. Methods 2.1 Glucosylation Reactions

Incorporation of LT-catalyzed [$^{14}C$] Glc in the GTPases or cell lysates, was performed as described by Just et al. Nature 375 (1995) 500–503) in the case of *C. difficile* toxin B. Briefly, 10 μl of UDP-[$^{14}C$] Glc in ethanol (0.2 μCi) (300 mCi/mmol Dupont-NEN, Les Ulis, France) was dried down under vacuum. Recombinant proteins (2 μg) dissolved in 15 μl of 50 mM triethanolamine-HCl buffer pH 7.5 containing 2 mM $MgCl_2$, 150 mM KCl, 100 μM DTT and 2 μM GDP, was added to the dried UDP-[$^{14}C$] Glc. LT (2 4 μg/ml) was then added to start the reaction which was carried out for 1 h at 37° C. The reaction was stopped by adding 5 μl of 2× SDS-sample buffer, boiled, and electrophoresed on a 15% SDS-PAGE. Upon staining with Coomassie blue followed by destaining, the gel was dried and radioactivity was recorded and counted using a phosphoimager system (Molecular Dynamic, Ca.). Glucosylation of HeLa cell lysates by LT was performed as followed; Hela cells (5×$10^6$) were homogenized by 3 cycles of freeze thawing in 200 μl of 50 mM Triethanolamine-HCl buffer pH 7.5 containing 100 μM DTT, 1 μg/ml leupeptin and pepstatin (glucosylation buffer). Cell lysates (20 μl) were added to 10 μl of dried UDP-[$^{14}C$] Glc, and 2 μg/ml of LT were added to start the enzymatic reaction. After 1 h at 37° C. further processing and imaging were done as described above.

2.2 "In vivo" Glucosylation by LT of Small GTP-Binding Proteins in Rat Fibroblasts Rat-1 fibroblasts (Rat-1-EJ-Rap2.31.A8) stably transfected with [$^{G12V}$] Ras and Rap2 (Jimenez, B., et al., Int. J. Cancer 49 (1991) 471–479) were grown in 60mm Petri dishes to a sub-confluent density. LT was added to the cells at the indicated concentration in 5 ml of fresh medium containing 10% FCS. After 2 h the cells were removed from the dishes with a rubber policeman and washed in 10 ml PBS followed by centrifugation at low speed. Washing was repeated 5 times to remove residual LT and finally the cell pellets were resuspended in 50 μl of glucosylation buffer. Cells were then lysed by 4 cycles of freeze-thawing. After homogenization, the amount of protein in each cell lysate was estimated. For "in vitro" glucosylation of small GTP-binding proteins with LT, 40 μl of cell lysate was added to 15 μl of dried UDP-[14] Glc with 5 μg/l of LT. This mixture was incubated for 1 h at 37° C. Then, 5 μl of each reaction was added to 10 μl of sample buffer, boiled and electrophoresed on a 15% SDS-PAGE. The gel was stained, destained, dried and analyzed for radioactivity by autoradiography.

2.3 Localization of the Glucosylated Amino-Acid in H-Ras

This experiment was performed by microsequencing the radioactively labeled protein. The H-Ras protein (10 μg) was first radioactively glucosylated by LT with 40 μl of dried UDP-[$^{14}C$] Glc (0.8 μCi) for 1 h, (reaction conditions as described above). Then, 10 mM unlabeled UDP-Glc was added, the reaction was further incubated for an additional 1 h at 37° C. and the proteins were separated on a 12.5% SDS-PAGE After migration, and staining by amidoblack, the band observed at 21 kDa was cut out from the gel and digested with 1 μg of trypsin in 200 μl of 100 mM Tris-HCl buffer pH 8.8 containing 0,01% Tween 20. The reaction was incubated 18 h at 35° C. The resulting peptides were separated by HPLC using a hydrophobic C18 column with an acetonitrile/trifluoroacetic gradient. Fractions eluted from the column were each analysed for radioactivity. Radioactive peptides were repurified by HPLC, using the C18 column with a sodium acetate buffer pH 6.00 gradient, The eluted peptides were analysed for radioactivity. The radioactive peaks were sequenced with a microsequencer (Applied Biosystem, Mass.) and the product of each Edman degradation cycle was collected and counted for radioactivity.

2.4 Immunofluorescence Experiments

Cells grown on coverslips were treated with LT and then fixed with 3% paraformaldehyde for 20 min. After fixation, monolayers were washed three times with PBS and free aldehyde groups were quenched by incubation with 50 mM $NH_4Cl$ in PBS for 10 min. Cells were permeabilized for 5 min at room temperature in PBS containing 0.2% Triton X100 and then incubated for 30 min at room temperature with the first antibody. Coverslips were then washed extensively with PBS and incubated with the secondary antibodies (Texas red-conjugated sheep anti-mouse (Amersham, UK)) together with FITC-Phalloidin (Sigma, L'Isle-d'Abeau, France) for 30 min. After 3 washes in PBS, coverslips were mounted in Moviol (Calbiochem-Behring, Germany) and fluorescence observed with a confocal microscope.

2.5 MAP-Kinases Activation

Experiments examining the effects of LT on epidermal growth factor (EGF)-stimulated MAP-kinases phosphorylation, were performed as follows: Swiss 3T3 cells were cultured according to routine procedures in H21 medium, supplemented with 10% FCS. When the cells reached confluency they were serum-starved overnight in 0.1% FCS. After 3 hours of incubation with LT (1.7 µg/ml) in serum free medium (the activity of LT was monitored by the cytopathogenic effect on cells), EGF was added (or not) at 50 ng/ml final concentration for 5 min. Cells were then scraped into PAGE sample buffer and 30 µg of total protein, for each experiment, was electrophoresed on 12.5% SDS-PAGE. The gel was blotted to nitrocellulose, and incubated with a monoclonal antibody directed against MAP-kinases (anti ERK1 and ERK2). Immune complexes were detected by horseradish peroxidase-conjugated secondary antibody, followed by the ECL kit (Amersham, UK).

2.6 Fluorescence Measurements

LT-catalysed glucosylation of ($[Y^{64W}]$Ras-GDP) was performed in 50 mM triethanolamine-HCl buffer pH 7.5 containing 140 mM KCl, 1 mM $MgCl_2$, 0.1 µM DTT. $[Y^{64W}]$Ras-GDP (50 µM) was incubated with 100 µM UDP Glc and 2.5 µg/ml LT at 37° C. for two hours. Control experiments were performed in the absence of LT.

Guanine nucleotide exchange and GTP hydrolysis of glucosylated versus unmodified $[Y^{64W}]$Ras (0.5 µM were measured at 37° C. in Hepes 50 mM, pH 7.5, $MgCl_2$ 1 mM and DTT 1 mM by monitoring tryptophan fluorescence at 340 nm upon excitation at 292 or 300 nm (12). When needed, 2 mM EDTA were added to reduce free magnesium to 0.8 µM.

2.7 Cell Microinjections

Diploid Chinese hamster lung fibroblasts (Don cells; ATCC No CCL 16=Don-wt) and the *C. difficile* toxins A and B resistant mutant of this cell line CdtR-Q (10, 11) here referred to as Don-Q, were grown on 13 mm slides for 48 h. Semiconfluent wildtype and mutant cells were microinjected (Eppendorf microinjector, Germany) with the indicated concentrations of LT, UDP-Glc or anti-LT antibodies with FITC-dextran (Sigma) in calcium-free PBS. Approximately 100 cells were microinjected in each experiment. The cultures were further incubated for 30 min. at 37° C. and fixed with 3.7% paraformaldehyde for 10 min. Cells were visualized by phase contrast and fluorescence microscopy.

3. Results

3.1 Disruption of Actin Stress-Fibers and Formation of Filopodia Induced in HeLa Cells by LT The cytopathic effect of *C. sordellii* LT consists of the rounding-up of cell bodies and profound alteration of F-actin containing structures (Popoff, M. R., Infect. Immun. 55 (1987) 35–43; Giry, M., et al., Infect. Immun. 63 (1995) 4063–4071). After a 3 h incubation with 2 µg/ml of LT, HeLa cells became round, displayed F-actin structures rearranged into cell surface filopodia, and exhibited a loss of actin stress-fibers. Using a polyclonal rabbit antibody which reacts against all known isoforms of the actin bundling protein fimbrin/plastin (Bretscher, A., and Weber, K., Proc. Natl. Acad. Sci. USA 78 (1981) 6849–6853), we observed that fimbrin/plastin was present in LT induced filopodia.

3.2 LT Catalyzes the UDP-Glc-Dependent Glucosylation of $M_r$ 21–23 kDa Proteins in Hela Cell Lysates Incubation of HeLa cell lysates with LT in the presence of UDP-$[^{14}C]$ Glc, followed by gel electrophoresis of the reaction products, showed that the toxin induced labelling of proteins in the $M_r$ range of 21–23 kDa FIG. 1). This reaction could be displaced by adding an excess of non radioactive UDP-Glc but not UDP-glucuronic acid (FIG. 1). No modification of proteins by LT was found with $[^{14}C]$ Glc alone.

3.3 LT Glucosylates Mr 21 kDa Proteins "in vivo"

To demonstrate that small GTP-binding proteins were glucosylated by LT "in vivo", Rat1-EJ-Rap2.31.A8 fibroblasts were incubated with increasing amounts of LT (from 0.005 to 5 µg/ml). The highest concentration of toxin caused the characteristic cytopathogenic effect of LT in 100% of the cells within 1 h. All cells were then lysed and the lysates were glucosylated with LT a second time, now "in vitro" in the presence of radioactive UDP-Glc. If LT acts from inside the cell, there should be an inverse correlation between the LT-dose used for "in vivo" pretreatment of cells and the amount of [14C]-Glc incorporated into small G-proteins "in vitro". As shown in FIG. 2, the highest rate of glucosylation by LT of a 23 kDa protein was observed in control cells. Two minor bands of 21 and 25 kDa glucosylated by LT, were also noticed in control lysates (FIG. 2). FIG. 2 also demonstrates that a clear decrease to a total absence of labelling of these bands was observed when the cells had been preincubated "in vivo" with increasing concentrations of LT prior to the "in vitro" LT glucosylation. Assuming that LT reacts with small G-proteins, in accordance with its homology to the *C. difficile* toxin B (Green, G. A., et al., Gene 161 (1995) 57–61), this dose-dependent activity of LT suggests that the toxin exerts its action from within the cell.

3.4 LT Glucosylates Ras, Rap, Ral and Rac Small GTP-Binding Proteins "in vitro"

Figure 3A:
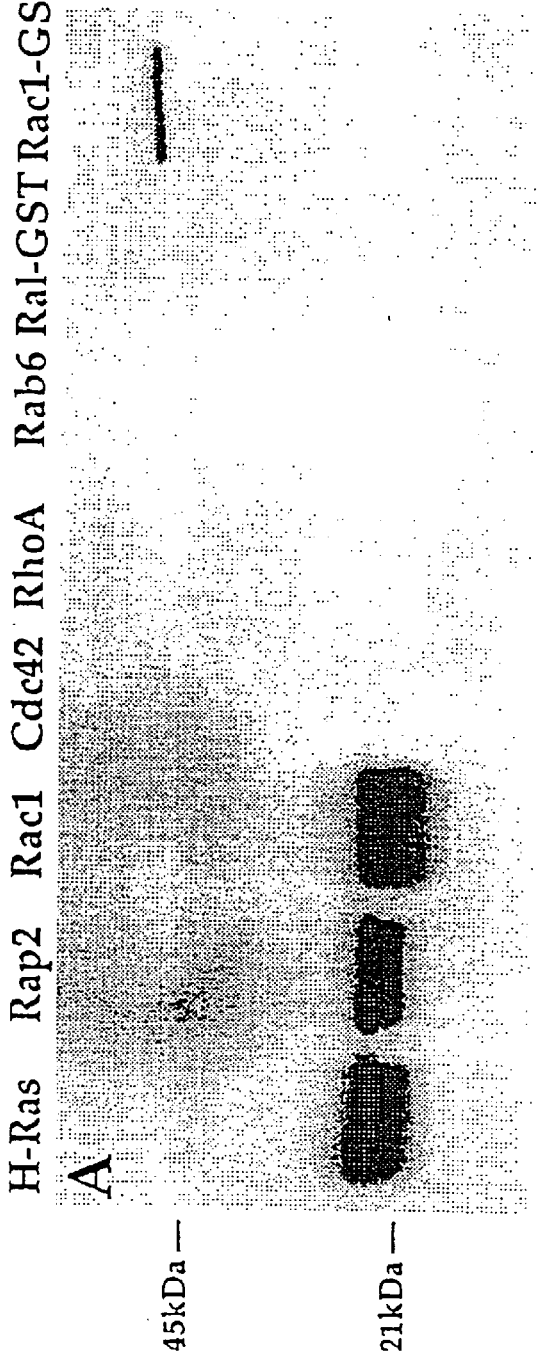
Figure 3A:
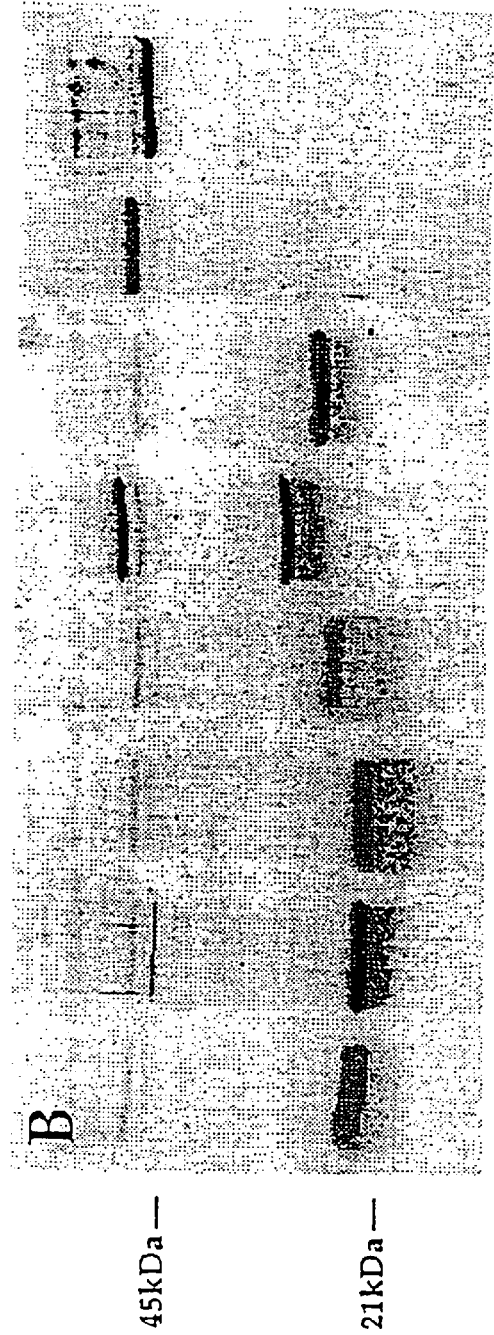
Figure 3B:

Specificity of LT was studied by incubating UDP-$[^{14}C]$ Glc and LT with different members of the p21 Ras superfamily of small GTP-binding proteins. As shown in FIGS. 3A and 3B, H-Ras, Rap2, Ral and Rac1 were substrates for LT catalysed glucosylation. In contrast, RhoA, Cdc42 and Rab6 were not modified "in vitro" by LT. First, Ral was used as a GST-fusion protein and remained unmodified by our lethal toxin preparation (FIG. 3A). However, when a Ral protein without protein fused to it was used as a substrate, LT modification of it was positive (FIG. 3B). Finally, no incorporation of glucose catalyzed by LT could be found on Arf1.

3.5 LT Glucosylates Threonine 35 of H-Ras

To identify the acceptor amino acid glucosylated by LT, H-Ras protein as modified by LT in the presence of UDP-$[^{14}C]$Glc, electrophoresed on SDS-PAGE, digested with trypsin and the resulting peptides were separated, as described in sections 1 and 2. As shown in FIG. 4, Panel 4-1A, 47 fractions were obtained. The radioactivity was exclusively associated with fractions 39 and 40. As shown in FIG. 4, Panels 4-2B and 4-2C, repurification of fraction 39 or 40 gave rise to a major peptide (D for 39 and E for 40) containing the radioactivity and several other small peptides. Peptides D and E were microsequenced and gave exactly the same amino-acid sequence. Each cycle of Edman degradation was collected and counted for radioactivity. The following unambiguous sequence was found for these peptides SALTIQLIQNHFVDEYDPTIEDSYR (SEQ ID NO.: 5). Cycle 19 corresponding to a threonine gave a very small signal. The small amount of threonine detected in position 19 may be the consequence of the LT catalyzed glucosylation of most of Ras molecules present in the reaction. Decrease or absence of threonine 37 Rho A in automated amino-acid sequencing, after glycosylation by toxin A or B, has been already reported (Just, I. et al., Nature 375 (1995) 500–503; Just, I., et al., J. Biol. Chem..270 (1995) 13932–13936). The amino-acid sequence found for both peptides D and E corresponds exactly to a sequence found in the H-Ras protein between amino-acids 17 to 41

(Barbacid, M., Ann. Rev. Biochem. 56 (1987) 779–827). Radioactivity was associated first with cycle 19 and decreased thereafter. The rise in radioactivity at cycle 19 establishes threonine 35 (of the H-ras molecule) as the unique amino-acid glycosylated by LT.

Figure 5:
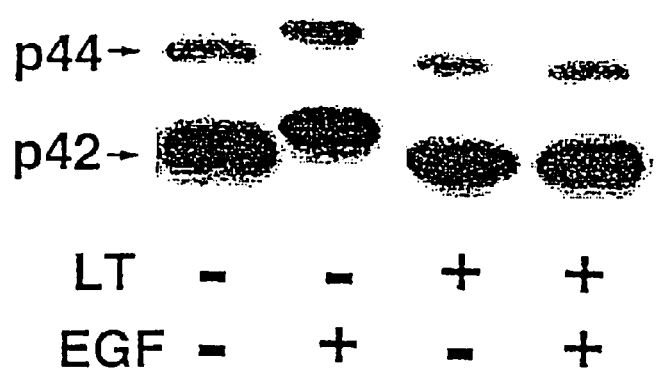

3.6 Inhibition of EGF-Induced Phosphorylation of MAP-Kinases in Swiss 3T3 Cells by LT In serum-starved Swiss 3T3 cells the mitogenic signalling pathway involving tyrosine phosphorylation of growth factor receptors such as EGF receptor and the subsequent Ras dependent activation of MAP-kinases phosphorylation is reduced to a basal level (Cobb, M. H., et al., Cell. Regul. 2 (1991) 965–978). After incubation with EGF, Ras dependent activation of MAP-kinases ERK1 and ERK2 can be followed by a shift in electrophoretic mobility resulting from phosphorylation (de Vries-Smits, A. M. M., Nature 357 (1992) 602–604). If the toxin blocks Ras activity, serum-starved Swiss 3T3 cells incubated with LT before the addition of EGF, should not activate MAP-kinases. As shown in FIG. 5, serum-starved Swiss 3T3 cells incubated with EGF, had MAP-kinases shifted toward higher molecular weight compared to MAP-kinases of cells not incubated with EGF. In contrast, when serum-starved Swiss 3T3 cells were incubated with LT, prior to incubation with EGF, the growth factor was not able to induce a shift in electrophoretic mobility of the P-kinases FIG. 5).

3.7 LT Acts in the Cytosol by Glucosylation

To further substantiate the notion that LT reaches the cytosol and acts by glucosylation of small GTP-binding proteins, a series of microinjection experiments was performed. Don-wt cells were incubated with LT in a medium containing non-immune rabbit serum. The expected characteristic cytopathogenic effect was observed in the whole cell population (FIG. 6A). When rabbit anti-LT antibodies were added to the medium the same amount of LT as used in FIG. 6A did not affect the cells (FIG. 6B). Drugs blocking the endocytic pathway acidification (Bafilomycin A1, Chloroquine or Monensin) known to prevent many bacterial toxins from penetration into the cytosol (Sandvig, K., et al., Biochem Soc. Transact. 20 (1992) 724–727), blocked the activity of LT on cells. When Don-wt cells in medium containing anti-LT antibodies were microinjected with LT they rapidly exhibited the cytopathogenic effect characteristic for LT (FIGS. 6C and D). Successful microinjection was monitored by a yellow-green fluorescence of fluorescein-dextran added to the solutions microinjected (see Materials and Methods). This showed that LT can exert its activity from the cytosol.

Figure 6:
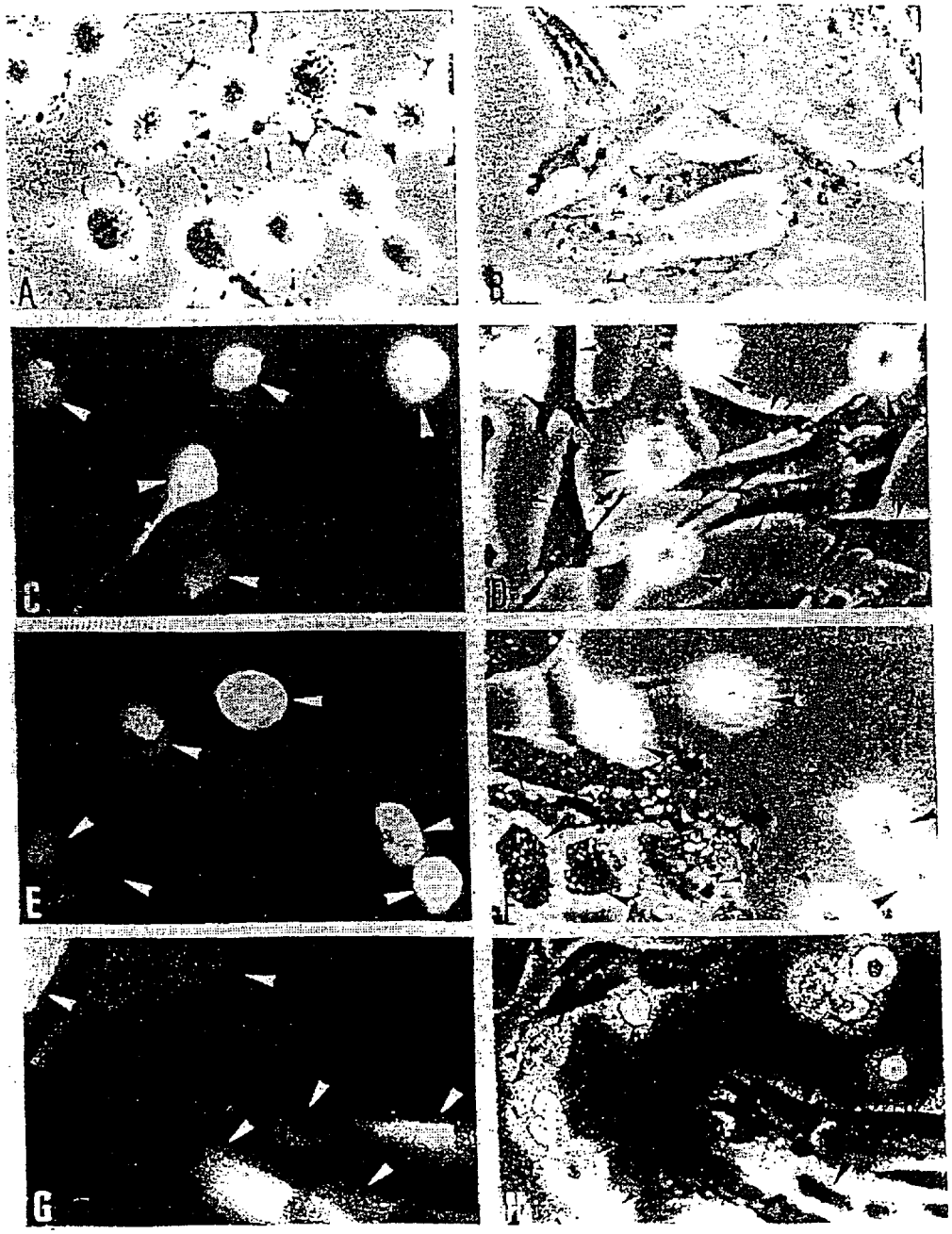

To demonstrate that the activity of LT is mediated through glucosylation (of G-proteins) advantage was taken of a mutant Don cell (Don-Q). This cell has a low content of UDP-Glc which renders it resistant to the glucosylating toxins A and B of C. difficile and also to LT (Chaves-Olarte, E., et al., J. Biol. Chem. (1996), in press). Don-Q cells were incubated with LT, followed by microinjection of UDP-Glc into some of them (those lighting up under fluorescence microscopy). As shown in FIGS. 6E and F, only cells which were microinjected with UDP-Glc exhibited the characteristic cytopathogenic effect of the toxin, suggesting that the toxin and the cofactor act at the same side of the cell membrane. The specificity of the effect was confirmed by microinjecting instead of TDP-Glc, UDP-Gal or UDP-GlcUA (100 mM) in cells similarly treated with LT. Neither of the additionally used activated sugars promoted any cytopathogenic effect. Finally, none of the three UDP-sugars used in this study had any effect if the cells were not pretreated with toxin. Knowing that our rabbit anti-LT serum neutralised the toxin, Don-wt cells were microinjected with this serum and then incubated with LT added to the medium. As shown in FIGS. 6G and H, microinjection of anti-LT antibodies protected against LT, clearly indicating that the neutralising antibody and the toxin meet each other in the cytosol. Accordingly, cells not injected exhibited the cytopathogenic effect typical of LT (FIGS. 6G and H), as did cells microinjected with non-immune rabbit serum. The experiments shown in FIG. 6 together with those presented in FIG. 2, show that LT acts from the cytosol by glucosylating small GTP-binding proteins, using UDP-Glc as a cofactor.

3.8 LT-Glucosylation of Ras Enhances GTP Dissociation Rate and Reduces GTP Hydrolysis of the GTP-Binding Protein The effects of LT glucosylation on the intrinsic properties of Ras was studied using the $[^{Y64W}]$Ras mutant. This mutant has the same intrinsic biochemical properties as wild-type Ras, but its activation-deactivation cycle can be followed in real time by monitoring changes in the fluorescence of tryptophan residue 64 (Antonny, B., et al., Biochemistry 30 (1991) 8287–8295). In FIG. 7A, $[^{Y64W}]$Ras-GDp, glucosylated or not, was first activated by the addition of GTP. After several minutes, the protein was converted again to the GDP-bound form by addition of a large excess of GDP. This experiment was performed at a low magnesium concentration, in order to favor the dissociation of the bound nucleotide (the rate limiting step of nucleotide exchange) and to prevent GTP hydrolysis. Similar fluorescence changes were observed for the unglucosylated and glucosylated forms of Ras (FIG. 7A). Indeed binding of GTP in place of GDP induced a decrease in fluorescence and conversely binding of GDP in place of GTP, an increase in fluorescence. Upon GTP addition, the time course of the fluorescence decrease was similar for the two forms of Ras, indicating that glucosylation did not greatly modify the GDP dissociation rate. In contrast, the increase in fluorescence by GDP addition was four time faster for the glucosylated Ras than for the unmodified Ras (FIG. 7A). This result demonstrates that glucosylation weakened GTP binding in the nucleotide site of Ras, by accelerating its dissociation rate. Similar effects of glucosylation were observed for the dissociation rate of GTPγS, either at low (1 μM) or high (1 mM) magnesium concentration.

The effect of glucosylation on GTP hydrolysis by Ras is shown in FIG. 7B. $[^{Y64W}]$Ras-GDP was incubated with GTP at 1 mM magnesium. Activation was triggered by the addition of 2 mM EDTA which reduced the free magnesium concentration below 1 μM The first instantaneous fluorescence decrease reflected the dissociation of magnesium from $[^{Y64W}]$Ras-GDP, whereas the slower fluorescence decrease reflected (as in FIG. 7A) the exchange of GTP for GDP. After completion of GDP/GTP exchange, magnesium was added back to the reaction (1 mM free magnesium). Due to the intrinsic GTPase activity of the protein, the fluorescence of the unmodified form of Ras slowly increased towards the level of fluorescence initially observed for Ras-GDP (FIG. 7B). In the case of the glucosylated form of Ras a much slower kinetics of GTPase activity was observed. Indeed, upon glucosylation of threonine 35 Ras had a four times slower intrinsic GTPase activity (FIG. 7B).

Glucosylation of $[^{Y64W}]$ Ras by LT slightly modified the fluorescence of the protein. As compared to unmodified $[^{Y64W}]$ Ras, LT glucosylated $[^{Y64W}]$Ras exhibited, on one hand, a larger absolute fluorescence level and, on the other hand, a smaller fluorescence change upon GDP/GTP exchange or GTP hydrolysis (FIG. 7A and 7B). Therefore, we looked for a fluorescence signal that could correlate with the glucosylation of the protein. When [$Y64W$] Ras-GDP was incubated with LT and UDP-Glc, fluorescence was enhanced by 2% within 2 hours (FIG. 7C). Since this signal required both LT and UDP-Glc, it certainly reflects the time course of UDP-Glc incorporation.

4. Production of Immunotoxins

Immunotoxins combine three parts: (1) a targeting device, specific for receptor molecules on the cell to be treated, (2) a translocation domain which enables the catalytic part (3) of the compound to cross the cell membrane.

The Catalytic Domain

Several catalytic domains of bacterial toxins have been used for constructing immunotoxins. The catalytic domain of such an immunotoxin hits an intracellular target of major importance for the cell, to be active in minimal amounts (ideally one molecule of enzyme per cell) finally blocking cell proliferation Targets may be the translation machinery and, our novel approach, reactions related to cell proliferation (such as transcription/signalling processes). Diphtheria toxin and Pseudomonas exotoxin A modify elongation factor (EF-2), thus blocking translation of mRNA into protein. LT of *C. sordellii* carries a novel catalytic principle in two respects: It is a glucosyltransferase, and it modifies the signal transducing small G-protein Ras, thus interfering with cell proliferation signals.

Diphtheria toxin and the P. exotoxin A have both successfully been used for constructing immunotoxins. Basically, their catalytic domain is amplified from the total DNA sequence by polymerase chain reaction (PCR) and then fused "in frame" to a targeting translocation device. The catalytic domain of LT is contained within the N-terminal 1020 amino acids of the molecule. Oligonucleotides (primers BCS1C (SEQ ID NO:1) and BCD2N (SEQ ID NO:2)) serve as 5'- and 3'-end primers for PCR amplification, respectively. These primers are elongated at both ends by small oligonucleotides of 8–12 base pair length which contain restriction sites allowing the in-frame cloning into the acceptor construct. The latter contains the targeting translocation device. Such acceptor constructs are the, cognate sequence of diphtheria toxin or of exotoxin A or parts thereof Cloning is in frame, such that a fusion protein is produced in *E. coli* that harbors both the catalytic glucosyltransferase and the targeting translocation device in a functional manner.

Such an immunotoxin has the target Ras inside the cell and this G-protein is inactivated by adding a glucose moiety into the effector domain at position threonine-35.

The catalytic domain is a defined N-terminal segment of LT which may replace catalytic domains in any other known immunotoxin such as the ADP ribosyltransferase catalytic domains of DT and ExoA. Replacing these catalytic segments can be achieved by either cutting the segment out of the DNA construct with restriction enzymes followed by integration of the appropriate LT catalytic domain, or by combined, separate PCR amplification of both the LT catalytic fragment and the targeting translocation device and then ligating these into a vector system finally allowing expression of the combined construct.

Targeting Translocation Device (T-T Device)

The targeting translocation device is taken from existing immunotoxin constructs such as immunotoxins derived from Diphtheria toxin or Pseudomonas exotoxin. The T-T device has the following properties: Firstly, it binds specifically to cells, differentiating between normal and tumor cells because of differential expression of the appropriate surface structure (receptor of hormones, cytokines, antigenic structure recognized by an antibody). Secondly, it mediates the transmembranal passage of the catalytic domain into the cytosol. Any such device can be used for targeting and translocation of the catalytic glucosyltransferase domain of LT into the cell, where the toxin acts.

In case of taking the translocation domain of LT (nucleotide sequences coding for approximately amino acids 1021–1700), the catalytic translocation domains of LT (nucleotide sequences coding for approximately amino acids 1–1700) are PCR-amplified (primers BCD2C (SEQ ID NO:3) and BCS3N (SEQ ID NO:4) for the translocation domain, or BCS1C and BCS3N for the catalytic translocation domains) allowing to obtain a combined catalytic translocation part in one segment. The targeting structure is then taken from the above mentioned sources, like hormones, growth factors, etc.

The immunotoxins may be produced in *E. coli* as fusion proteins or as recombinant *E. coli* proteins in separate parts, followed by chemically combining the different segments in the "test tube", both according to methods described and known.

PCR primers of the catalytic domain are BCS1C (SEQ ID NO:1) and BCD2N (SEQ ID NO:2).

PCR primers of the translocation domain are BCD2C (SEQ ID NO:3) and BCS3N (SEQ ID NO: 4).

As PCR primers for the catalytic and translocation domains, BCS1C and BCS3N are used, as a primer pair.

LIST OF REFERENCES

Allured, V. S., et al., Proc. Natl. Acad. Sci. USA 83 (1986) 1320–1324
Antonny, B., et al., Biochemistry 30 (1991) 8287–8295
Arseculeratne, S. N., et al., J. Med. Microbiol. 2 (1969) 37–53
Atlas, I., et al., Cancer Res. 52 (1992) 3335–3339
Barbacid, M., Ann. Rev. Biochem. 56 (1987) 779–827
Batra, J. K., et al., Proc. Natl. Acad. Sci. USA 89 (1992) 5867–5871
Bette, P., et al., Toxicon 29 (1991) 877–887
Bretscher, A., and Weber, K., Proc. Natl. Acad. Sci. USA 78 (1981) 6849–6853
Brinkmann et al., Proc. Natl. Acad. Sci. USA 90 (1993) 7538–7542
Brinkmann, et al., Proc. Natl. Acad. Sci. USA 89 (1992) 3075–3079
Carrel, S., et al., Eur. J. Immunol., 16 (1986) 649–652
Chaves-Olarte, E., et al., J. Biol. Chem. (1996), in press
Choe, S., et al., Nature 357 (1992) 216–222
Cobb, M. H., et al., Cell. Regul. 2 (1991) 965–978
de Vries-Smits, A. M. M., Nature 357 (1992) 602–604
EMBL DataBank Accession No. X82638
EP-B 0 194 276
Giry, M., et al., Infect. Immun. 63 (1995) 4063–4071
Goldenberg, et al., J. Clin. Oncology 9 (1991) 548–568
Green, G. A., et al., Gene 161 (1995) 57–61
Hall, A., Ann. Rev. Cell. Biol. 10 (1994) 31–34
Harwerth, I.-M., et al., J. Biol. Chem. 21 (1992) 15160–15167
Herrmann, C., et al., J. Biol. Chem. 270 (1995) 2901–2905
Humphrey, P. A., et al., Proc. Natl. Acad. Sci USA 87 (1990) 4207–4211
Jimenez, B., et al., Int. J. Cancer 49 (1991) 471–479
John, J., et al., J. Biol. Chem. 268 (1993) 923–929
Just, I., et al., J. Biol. Chem. 269 (1994) 10706–10712
Just, I., et al., J. Biol. Chem. 270 (1995) 13932–13936
Just, I., et al., J. Clin. Invest. 95 (1995) 1026–1031
Just, I., et al., Nature 375 (1995) 500–503

Kalofonos, H. P., et al., J. Nucl. Med. 30 (1989) 1636–1645
Kaminski, et al., New England Journal of Medicine 329 (1993) 459–465
Kasprzyk, P. G., et al., Cancer Res. 52 (1992) 2771–2776
Kohl, N. E., et al., Science 260 (1993) 1934–1937
Levitzky, A., Euro. J. Biochem. 226 (1994) 1–13
Lyerly, D. M., et al., Clin. Microbiol. Rev. 1 (1988) 1–18
Madaule, P., and Axel, R., Cell 41 (1985) 31–40
Martinez, R. D., and Wilkins, T. D., J. Med. Microbiol. 36 (1992) 30–32
Monoclonal Antibodies in Clinical Medicine, ed. McMichael, A. J., and Fabre, J. W., Academic Press, London (1982) 168–192
Montecucco, C., and Schiava, G., Trends Biochem. Sci. 18 (1993) 324–326
Nassar, N., et al., Nature 375 (1995) 554–560
Nobes, C. D., and Hall, A., Cell 81 (1995) 53–62
Pai, E. F., et al., EMBO J. 9 (1990) 2351–2359
Popoff, M. R., Infect. Immun. 55 (1987) 35–43
Press, et al., New England Journal of Medicine 329 (1993) 1219–1224
Press, O. W., et al., J. Clin. Onc. 7 (1989) 1027–1038
Prior, T. I., et al., Biochemistry 31 (1992) 3555–3559
Razakis-Adocke, M., et al., Nature 363 (1993) 83–85
Reinherz, E. L., et al., Immunol Rev. 74 (1983) 83–112
Ridley, A. J., et al., Cell 70 (1992) 401–410
Sandvig, K., et al., Biochem Soc. Transact. 20 (1992) 724–727
Segal, M., et al., Proc. Natl. Acad. Sci. USA 90 (1993) 5564–5568
Shirasawa et al., Science 260 (1993) 85–88
Sullivan, N. M., et al., Infect. Immun. 35 (1982) 1032–1040
U.S. Pat. No. 4,947,778
U.S. Pat. No. 5,091,513
U.S. Pat. No. 5,132,405
von Eichel-Streiber, C., et al., Microbiol. Pathogenesis 2 (1987) 307–318
von Eichel-Streiber, C., et al., Mol. Microbiol. 17 (1995) 313–321
von Eichel-Streiber, C., et al., Trends in Microbiology 4 (October 1996) 375–382
Wels, W., et al., Cancer Res. 52 (1992) 6310–6317
Welt, S., et al., J. Clin. Oncol. 8 (1990) 1894–1906
White, M. A., et al., Cell 80 (1995) 533–541
WO 88/01649
WO 88/09344
WO 94/04696
WO 94/22476

What is claimed is:

1. An isolated polypeptide fragment of *Clostridium sordellii* lethal Toxin (LT) with glucosyltransferase activity consisting of N-terminal amino acids 1–1020 of SEQ ID NO:6.

2. An isolated compound consisting of N-terminal amino acids 1–1020 of SEQ ID NO:6 chemically coupled to an antibody which permits the compound to bind to a target cell.

3. An isolated compound consisting of N-terminal amino acids 1–1700 of SEQ ID NO:6 chemically coupled to an antibody which permits the compound to bind to a target cell.

4. A composition consisting of a compound according to claim 2 or 3 and a pharmaceutically acceptable adjuvant or carrier.

5. A method of manufacturing a composition, said method comprising the steps of bringing together a compound according to claim 2 or 3 and a pharmaceutically acceptable adjuvant or carrier.

* * * * *